(12) United States Patent
Wilk

(10) Patent No.: US 6,678,403 B1
(45) Date of Patent: Jan. 13, 2004

(54) METHOD AND APPARATUS FOR INVESTIGATING INTEGRITY OF STRUCTURAL MEMBER

(76) Inventor: Peter J. Wilk, 185 W. End Ave., New York, NY (US) 10023

( * ) Notice: Subject to any disclaimer, the term of this patent is extended or adjusted under 35 U.S.C. 154(b) by 581 days.

(21) Appl. No.: 09/661,521

(22) Filed: Sep. 13, 2000

(51) Int. Cl.[7] .................................................. G06K 9/00
(52) U.S. Cl. ........................................ 382/152; 73/644
(58) Field of Search ................................. 382/141, 152; 702/34; 73/1.82, 570, 570.5, 584, 587, 644; 367/87, 88, 7, 118; 181/0.5, 101; 128/647, 660

(56) References Cited

U.S. PATENT DOCUMENTS

| | | | |
|---|---|---|---|
| 3,585,577 A | 6/1971 | Rollwitz | 367/90 |
| 3,603,303 A | * 9/1971 | Stouffer | 600/437 |
| 4,197,591 A | 4/1980 | Hagemann | 367/6 |
| 4,319,347 A | 3/1982 | Savit | 367/52 |
| 4,403,311 A | 9/1983 | Tournois | 367/11 |
| 4,719,426 A | 1/1988 | Weiss | 324/345 |
| 4,727,329 A | 2/1988 | Behr | 324/345 |
| 5,025,423 A | 6/1991 | Earp | 367/137 |
| 5,128,904 A | 7/1992 | Chambers | 367/129 |
| 5,136,550 A | 8/1992 | Chambers | 367/38 |
| 5,184,330 A | 2/1993 | Adams et al. | 367/111 |
| 5,200,931 A | 4/1993 | Kosalos et al. | 367/88 |
| 5,323,683 A | 6/1994 | Dilhan et al. | 89/1.13 |
| 5,438,552 A | 8/1995 | Audi et al. | 367/88 |
| 5,452,639 A | 9/1995 | Aulenbacher et al. | 89/1.13 |
| 5,471,435 A | 11/1995 | Marschall | 367/135 |
| 5,563,848 A | 10/1996 | Rogers et al. | 367/99 |
| 5,617,031 A | 4/1997 | Tuttle | 324/326 |
| 5,671,136 A | 9/1997 | Willhoit, Jr. | 702/18 |
| 5,672,825 A | 9/1997 | Uno et al. | 73/579 |
| 5,808,969 A | 9/1998 | Arnaud et al. | 367/103 |
| 5,930,199 A | 7/1999 | Wilk | 367/88 |
| 6,002,644 A | 12/1999 | Wilk | 367/88 |
| 6,055,212 A | 4/2000 | Wilk | 367/68 |
| 6,055,214 A | 4/2000 | Wilk | 367/99 |
| 6,138,515 A | * 10/2000 | Moufle et al. | 73/639 |
| 6,298,727 B1 | * 10/2001 | Fleming et al. | 73/644 |

FOREIGN PATENT DOCUMENTS

| | | | |
|---|---|---|---|
| GB | 2 085 591 A | | 10/1981 |
| JP | 63-61161 | * | 3/1988 |
| WO | WO 99/51995 | | 10/1999 |

OTHER PUBLICATIONS

IBM Technical Disclosure Bulletin, Flexible Acoustic Probe Utilizing Thermoelastic Expansions vol. 22, issue 3, pp 1298–1300, 1979.*

* cited by examiner

Primary Examiner—Samir Ahmed
(74) Attorney, Agent, or Firm—R. Neil Sudol; Henry D. Coleman; William J. Sapone

(57) ABSTRACT

A method for investigating structural integrity utilizes a carrier member having a flexible surface and a plurality of electromechanical transducer elements attached to the carrier member, the transducer elements being spaced from each other along at least two spatial dimensions. The method includes conforming the flexible surface to a solid structural member, so that a substantial portion of the flexible member is in effective wave-transmitting engagement with the structural member, thereafter transmitting pressure waves from at least one of the transducer elements into the structural member, receiving pressure waves reflected from an internal structural defect in the structural member in response to the pressure waves transmitted from the one of the transducer elements, and analyzing the received pressure waves so as to detect the structural defect.

28 Claims, 17 Drawing Sheets

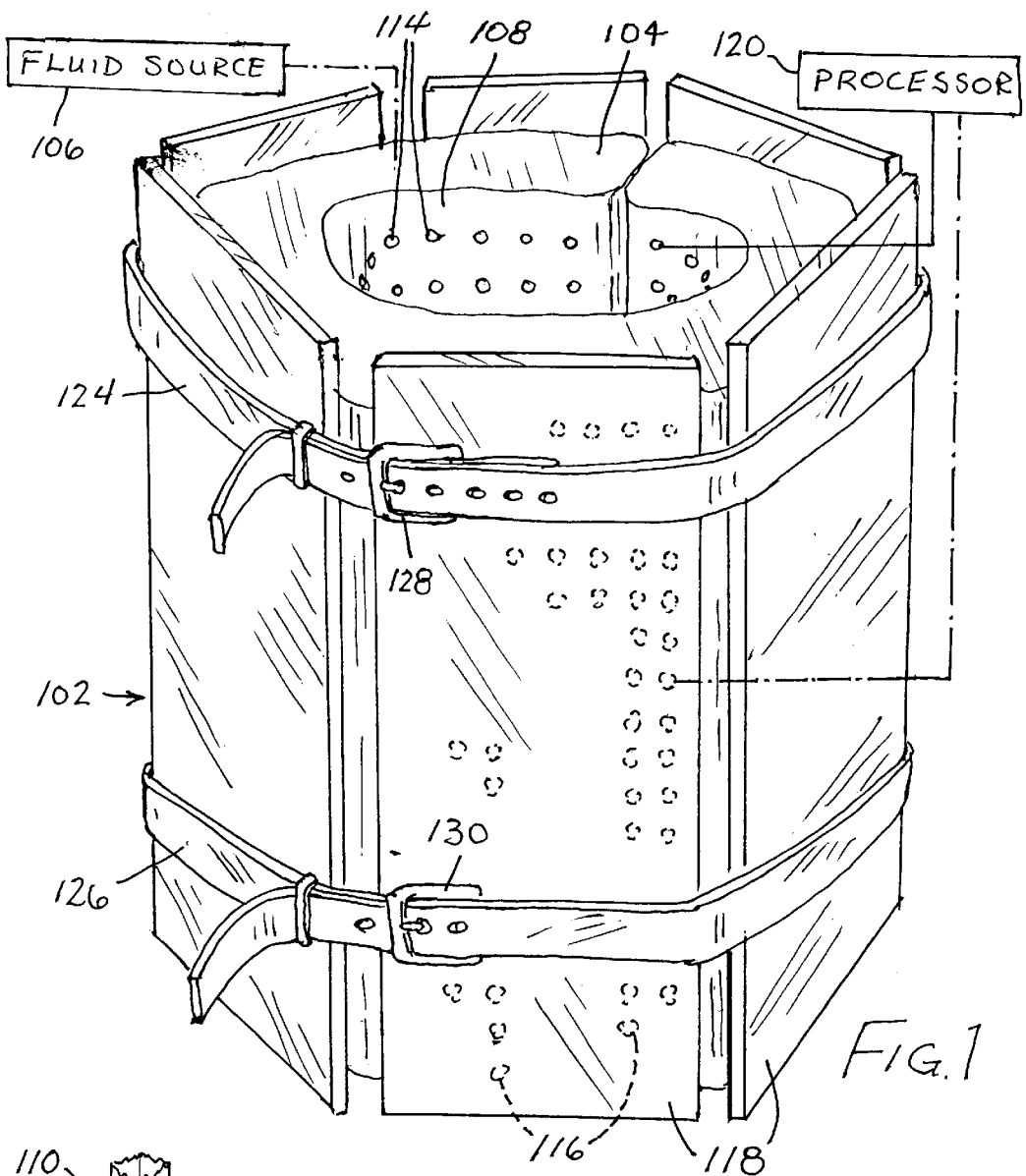
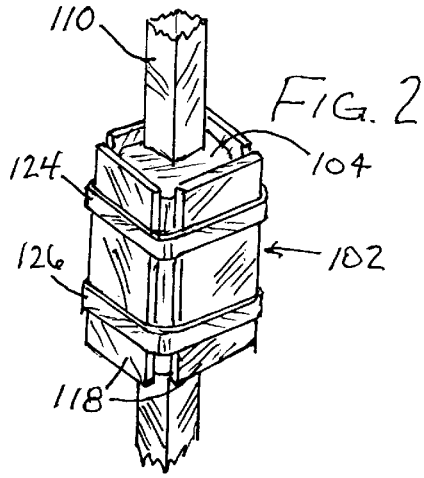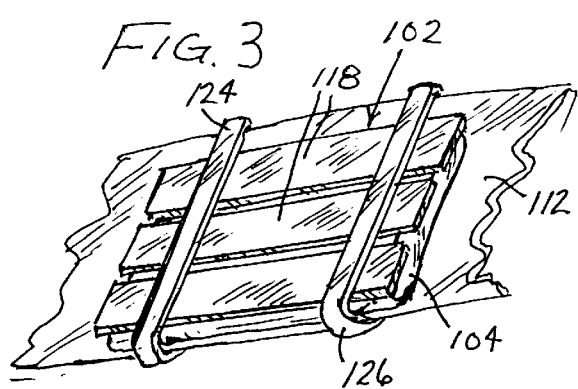

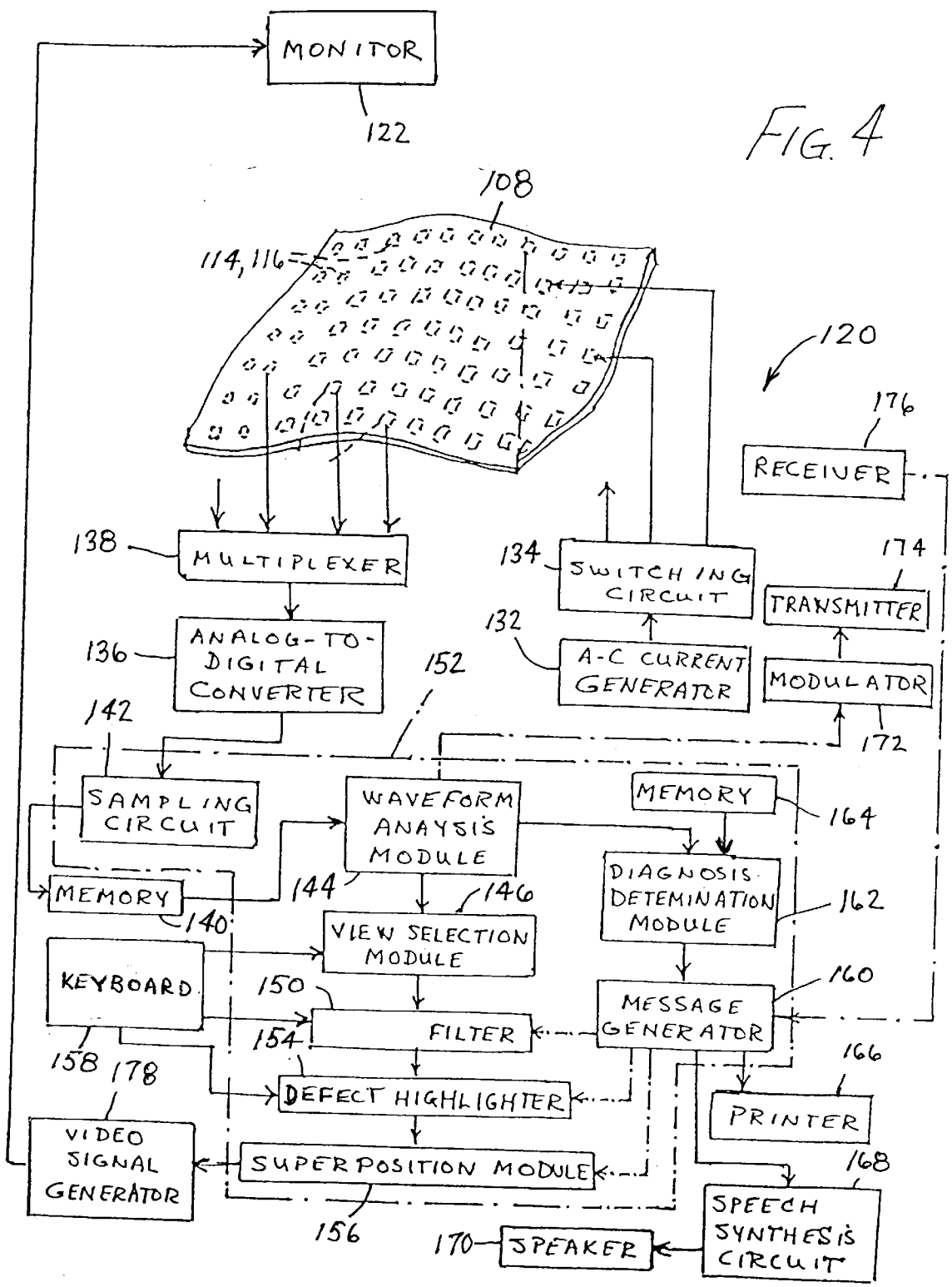

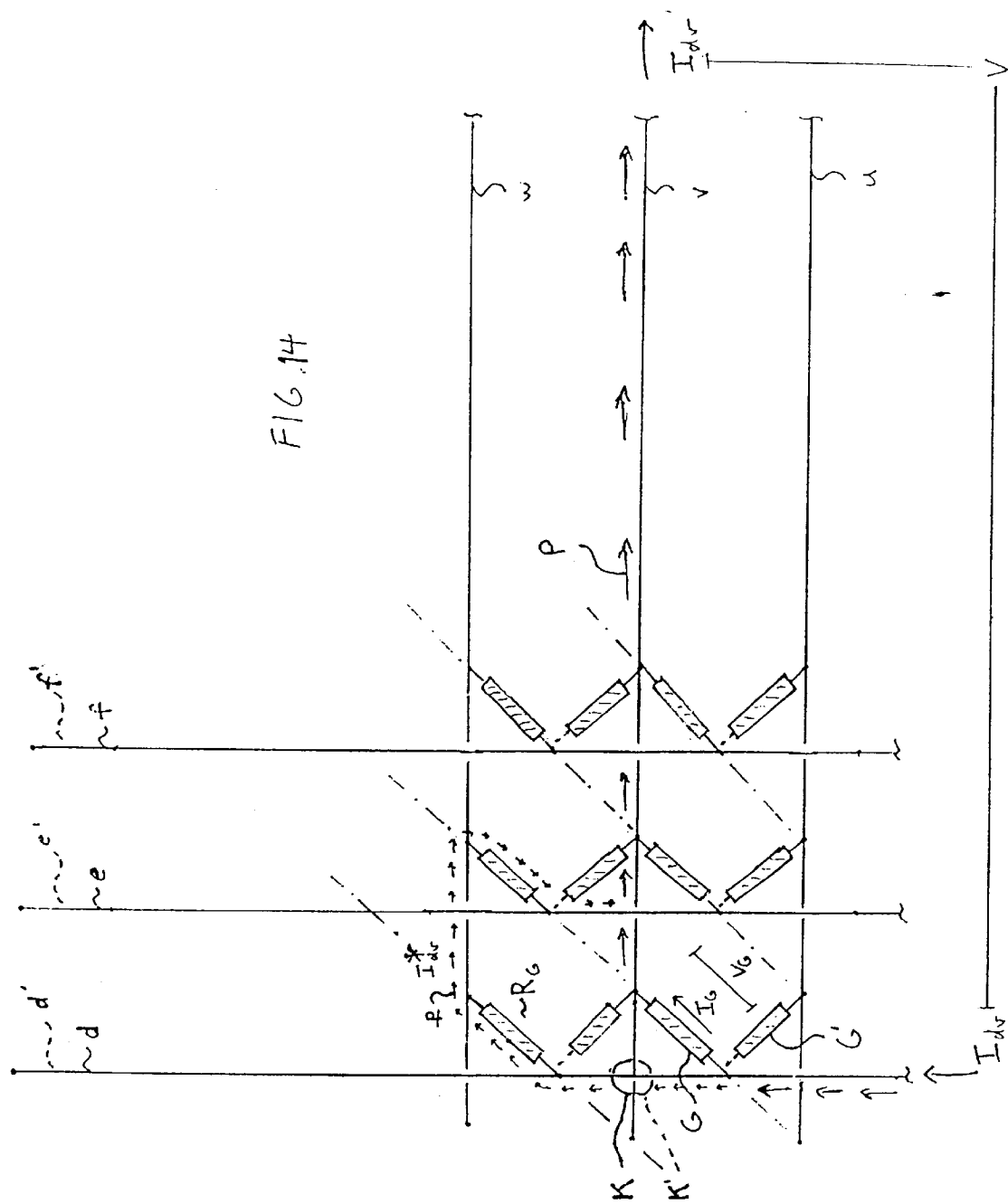

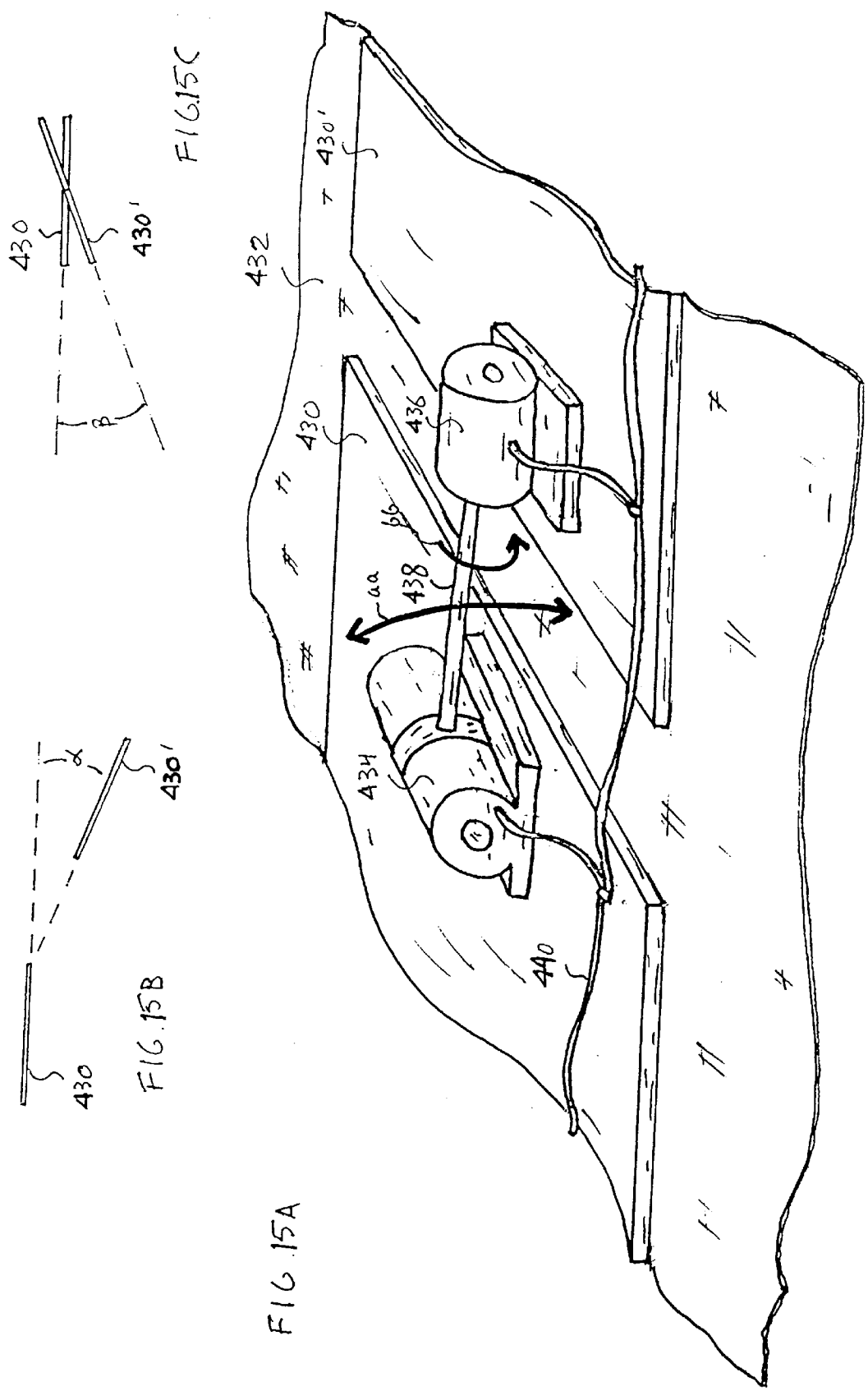

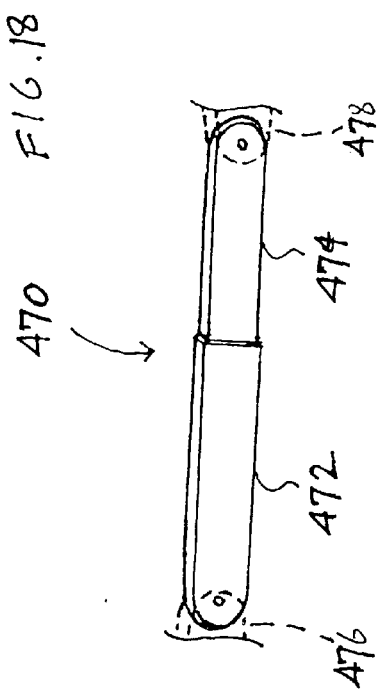
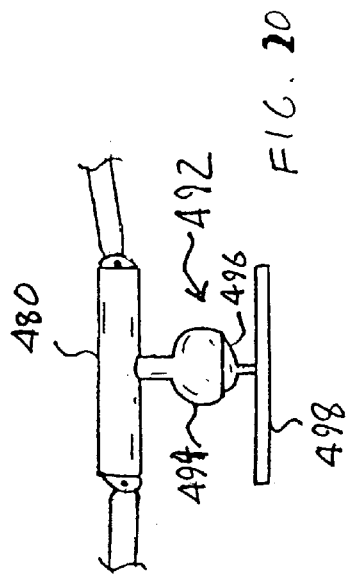
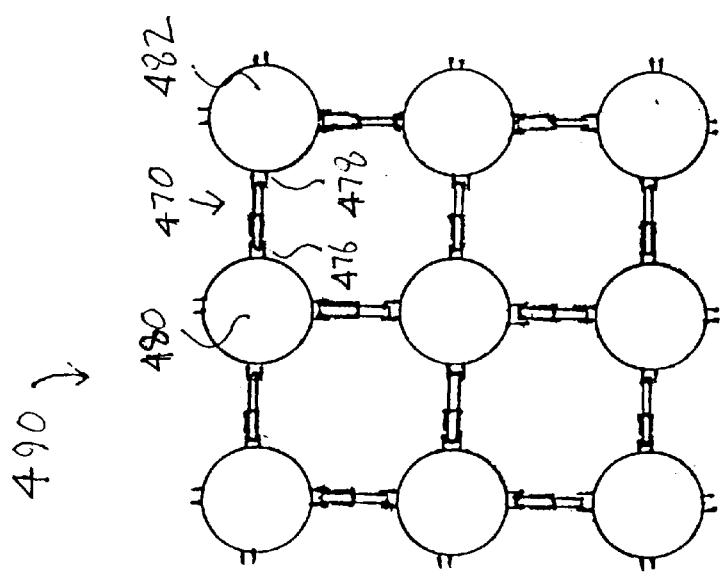

METHOD AND APPARATUS FOR INVESTIGATING INTEGRITY OF STRUCTURAL MEMBER

BACKGROUND OF THE INVENTION

This invention relates to a method and also to an associated apparatus for examining structural members for purposes of detecting hidden defects.

Architectural and vehicular structural members such as bridge girders, columns, floor and roof support beams, airplane wings, and other architectural and vehicular stress-bearing members can suffer failure arising from invisible defects. Not infrequently, stress fractures and fatigue cracks originate internally to a support member and are not detectible even by the most sensitive and rigorous of existing testing techniques. Such defects may result in dangerous, even fatal, accidents irrespective of the diligent care taken by maintenance personnel.

It is not uncommon for aging structures to be destroyed or discarded for fear of structural failure even though the structures may still have many years of useful life, unbeknownst to the owners. This premature retirement of buildings, bridges, planes, train cars, etc., is generally a waste of public and private assets and thus contributes to rising costs and depleting resources.

Even where architectural and vehicular assets are maintained, structural investigations are time consuming and expensive. The necessary expense is particularly evident where the investigated structures must be disassembled and transported to testing facilities. Detecting hidden defects without disassembly of the structures is even more difficult when the structures cannot be disassembled, for example, in the cases of buildings and bridges.

SUMMARY OF THE INVENTION

A method for investigating structural integrity in accordance with the present invention utilizes a carrier member having a flexible surface and a plurality of electromechanical transducer elements attached to the carrier member, the transducer elements being spaced from each other along at least two spatial dimensions. The method comprises conforming the flexible surface to a solid structural member, so that a substantial portion of the flexible member is in effective wave-transmitting engagement with the structural member, thereafter transmitting energization or diagnostic pressure waves into the structural member, receiving pressure waves reflected from an internal structural defect in the structural member in response to the pressure waves transmitted into the structural member, and analyzing the received pressure waves so as to detect the structural defect.

Pursuant to another feature of the present invention, the method further comprises generating a signal encoding an image of the structural defect from the analyzed pressure waves and presenting the image on a display. It is contemplated that the analyzing of the incoming or reflected pressure waves is implemented by operating a specially programmed general-purpose or dedicated digital computer. That computer may be further operated to highlight a selected feature of the structural defect on the display. The highlighting of the structural defect may include varying video image intensity in a portion of a video image on the display. In addition, the computer may be operated to select the displayed image from among a multiplicity of possible images of the structural defect. For instance, the structural defect may be viewed from any of a number of different angles and magnifications. Parts of the defect may be stripped away or filtered out to enable viewing of internal parts of the defect.

These functions are carried out in part by analyzing the incoming or reflected pressure waves to construct a three-dimensional electronic model or analog of the detected structural defect. The electronic model or analog may then be manipulated by conventional three-dimensional programming to rotate the defect about three Cartesian axes and to magnify the defect in whole or in part.

In order to detect a microscopic defect, the incoming or reflected pressure waves are processed to construct any microscopic structures in the memory of the computer. Detected microscopic structures are then analyzed, for example, by pattern recognition techniques and mathematical operations to determine whether the structures are potential sources of structural failure. Thus, the analyzing of the received pressure waves includes operating the computer to perform an automated diagnosis or evaluation of the structural defect based in part on the digital or electronic model of the structural defect. The performance of the automated diagnosis or evaluation of the structural defect may include operating the computer to automatically compare the digital or electronic model with digital or electronic models of known structural defects stored in a memory of the computer. Any suspect structural anomalies may be reported to a user, for instance, by the display, by print-out, audible signal, etc.

In accordance with another feature of the present invention, the carrier member includes a flexible web. The flexible surface is a surface of the web, the conforming of the flexible surface to the structural member including the step of wrapping the web around at least a portion of the structural member. Where the transducer elements are mounted to the web, the conforming of the flexible surface to the structural member includes placing the transducer elements in contact with the structural member. This procedure is especially effective when the structural member has a substantially smooth outer surface.

An apparatus, described in detail below, for carrying out the method of the invention, is easily portable. Moreover, in testing a large structural member such as a bridge girder or airplane wing, the carrier member is simply removed from one section of the structural member and reapplied to another section of the structural member until essentially the entire member has been examined.

Where the carrier member includes at least one substantially rigid panel and a flexible web connected to the panel to form a bag along the panel, the flexible surface being a surface of the web, the conforming of the flexible surface to the structural member includes (a) placing the flexible web in contact with the structural member and (b) feeding a fluid to the bag to press the web against the structural member. In this procedure, where the transducer elements are mounted to the web, the conforming of the flexible surface to the structural member also includes placing the transducer elements in contact with the structural member.

Where the panel is one of a plurality of panels of the carrier member, the conforming of the flexible surface to the structural member includes (i) placing the bag so that the flexible surface faces the structural member and so that the panels are disposed on an outer side of the bag, away from the structural member and (ii) fastening the panels to one another about the structural member to limit expansion of the bag upon feeding of the fluid thereto. Thus, the panels serve as a restraint ensuring an effective pressure-wave transmitting contact between the flexible surface of the bag and the structural member. It is to be noted in this regard that at least some of the transducer elements may be disposed on the panel. In that case, the fluid fed to the bag is a liquid, so that the transmitting of the pressure waves from at least one of the transducer elements into the structural member includes transmitting the pressure waves through the liquid in the bag. The liquid may thus serve not only a pressurizing function but also as a medium for pressure wave transmission.

The fastening of the panels of the carrier member about the bag and concomitantly about a section of the structural member may be implemented by any suitable means including, but not limited to, straps, clasps, buckles, hook and loop fasteners (VELCRO™), and hooks and eyelets. Generally, the panels are fastened about the structural member prior to pumping or siphoning of liquid into the bag.

It is contemplated that many structural members to be tested by the method and apparatus of the present invention will have several sides extending at angles with respect to one another. In such a case, the conforming of the flexible surface to the structural member includes placing the flexible surface in engagement with at least two surfaces of the structural member extending at a substantial angle relative to one another.

The pressure waves transmitted into the structural member and received as reflections from internal substructures thereof may have a plurality of different frequency ranges. The different frequency ranges have different penetration characteristics, as well as different resolving powers. The use of different frequency ranges provides a greater amount of raw data for analysis and diagnosis of internal irregularities of structural members.

Where the transducer elements are mounted to the carrier member in a predetermined array, the method may further comprise the step of energizing the transducer elements in a predetermined sequence.

An apparatus for investigating defects in structural members comprises, in accordance with the present invention, a carrier member having a flexible surface, the carrier member including a pressurizable bag for conforming the flexible surface to a solid structural member so that a substantial portion of the flexible member is in effective wave-transmitting engagement with the structural member. The apparatus additionally comprises a plurality of electromechanical transducer elements attached to the carrier member, the transducer elements being spaced from each other along at least two spatial dimensions. A frequency generator is operatively connected to at least a given one of the transducer elements for energizing that given transducer element to transmit pressure waves into the structural member. A frequency processor is operatively connected to at least another one of the transducer elements to process pressure waves received by that other transducer element from an internal structural defect in the structural member in response to the pressure waves transmitted from the given transducer element. The processor includes means for analyzing the received pressure waves to detect the structural defect.

Pursuant to another feature of the present invention, the apparatus further comprises an expansion restrictor surrounding the bag for limiting outward expansion thereof in a direction opposite the structural member. As described above, the expansion restriction may include a plurality of rigid panels movably connected to one another and locks or fasteners operatively connected to the panels.

According to another aspect of the invention, the apparatus also comprises an imaging component generating a signal encoding an image of the structural defect from the analyzed pressure waves, the imaging component being operatively connected to a display for presenting the image to a viewer or operator.

The processor preferably includes generic digital processing circuits modified by programming for deriving a digital or electronic model of the structural defect from the analyzed pressure waves. The process may additionally include programming-modified generic digital processing circuits for executing an automated diagnosis or evaluation of the structural defect based in part on the digital or electronic model of the structural defect.

The transducer elements may be all mounted to the bag along a flexible panel thereof, all mounted to rigid panels, or partially mounted to a flexible panel and a rigid panel. Where the transducer elements are attached to a flexible web, at least some of the transducers are placed directly in contact with the structural member under test.

It will be recognized that the processor or wave analyzer must be provided with data from which the relative positions of the transducer elements can be ascertained. This data may be generated by a separate system of position sensors or from signals generated and sensed by the transducer elements themselves.

The present invention facilitates an examination of structural members such as bridge girders, columns, floor and roof support beams, airplane wings, and other architectural and vehicular stress-bearing structures. An apparatus and a related method for investigating integrity of structural members in accordance with the present invention enables the detection and identification of sources of potential structural failure, even where those sources are only in their nascent stages of development.

An apparatus and an associated method for investigating integrity of structural members in accordance with the present invention is portable and utilizable in many applications in situ, without necessitating a deconstruction or disassembly of the structure being investigated. A structural examination or investigation as contemplated herein facilitates the maintenance of architectural and vehicular bodies, reduces costs of investigation, and enables a differentiation of different defects or structural irregularities.

BRIEF DESCRIPTION OF THE DRAWINGS

FIG. 1 is partially a schematic perspective view and partially a block diagram of a system or apparatus for carrying out structural integrity investigations in accordance with the present invention.

FIG. 2 is a partial schematic perspective view showing a use or application of the apparatus of FIG. 1.

FIG. 3 is a partial schematic perspective view showing another use or application of the apparatus of FIG. 1.

FIG. 4 is essentially a block diagram of functional electronic and signal processing components of the apparatus of FIG. 1.

FIG. 14 is a partial circuit diagram of a second system of strain gauges.

FIG. 15A is a schematic perspective view of a mechanical linkage and encoding device utilizable as a sensor position determination system in an acoustic imaging device.

FIG. 15B is a diagram showing a first definition of an angle with respect to the linkage of FIG. 15A.

FIG. 15C is a detail showing a second definition of an angle with respect to the linkage of FIG. 15A.

FIG. 18 is a schematic perspective view of a single linkage of a second mechanical armature utilizable in a sensor position determination system in an acoustic imaging device.

FIG. 19 is a schematic plan view of a second mechanical armature utilizing the linkage of FIG. 18.

FIG. 20 is a detail elevation showing a modification of the armature of FIG. 19 for incorporation of additional mechanical degrees of freedom.

FIG. 23B is a block functional diagram of a chip-level logic optical sensor.

DETAILED DESCRIPTION

Figure 5:
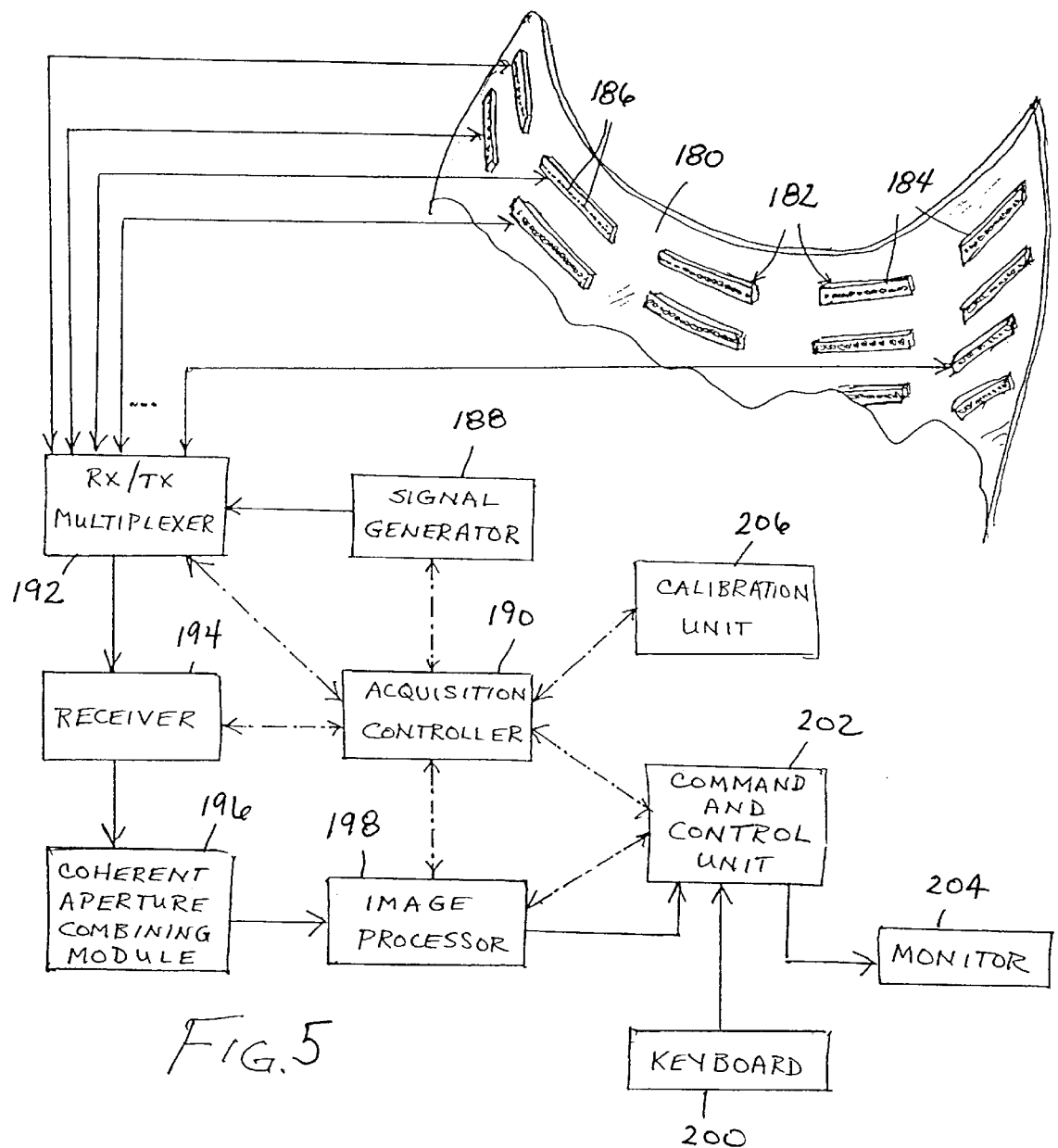
FIG. 5 is partially a schematic perspective view and partially a block diagram of an ultrasonic imaging componentry utilizable in the apparatus of FIG. 1 in accordance with the present invention.
Figure 6:
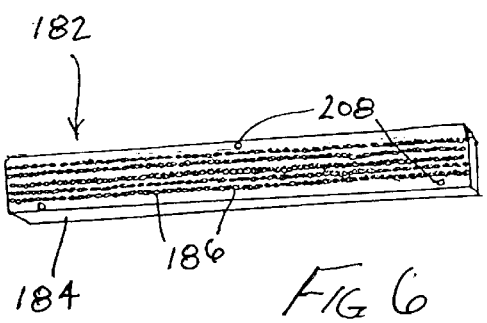
FIG. 6 is a schematic perspective view, on a larger scale, of a modular transducer package or array aperture included in the system of FIG. 5.

FIG. 1 schematically depicts an apparatus utilizable in seeking, detecting, displaying, and evaluating defects in structural members such as bridge girders, columns, floor and roof support beams, airplane wings, and other architectural and vehicular stress-bearing members. The investigatory apparatus of FIG. 1 comprises a carrier 102 having a bag 104 pressurizable with a gas such as air or a liquid such as water from a fluid source 106. When expanded or filled with fluid, bag 104 exerts pressure on a flexible web or surface 108 to conform the flexible web to a solid structural member such as a steel girder or concrete beam 110 (FIG. 2) or a metal web such as an airplane wing 112 (FIG. 3). Bag 104 thus ensures that a substantial portion of the flexible web 108 is in effective wave-transmitting engagement with the structural member under investigation.

As further illustrated in FIG. 1, the integrity investigatory apparatus additionally comprises a plurality of electromechanical transducer elements 114 attached to carrier 102, the transducer elements being spaced from each other along at least two spatial dimensions. Alternatively or additionally, similar spaced electromechanical transducer elements 116 are disposed on one or more of a plurality of rigid panels 118 included in carrier 102 and attached to bag 104. More specifically, transducer elements 114 and 116 include at least one and preferably a multiplicity of piezoelectric electroacoustic transducers (not separately designated) acting as ultrasonic pressure wave generators for transmitting ultrasonic pressure waves into a structural member under investigation. Transducers elements 114 and 116 further include at least one and preferably a multiplicity of piezoelectric acoustoelectric transducers (not separately designated) acting as ultrasonic pressure wave receivers or sensors for detecting incoming ultrasonic pressure waves reflected from internal structural irregularities of the structural member.

Transducer elements 114 are attached to web 108 for disposition directly in contact with a structural member under investigation. The pressurization of bag 104 by source 106 presses transducers 114 against the structural member to ensure the efficacy of mechanical or pressure wave transmission into the structural member. Transducer elements 116 generally require that bag 104 is filled with a liquid so that ultrasonic pressure waves generated by electroacoustic transducers on panels 118 are transmitted into the structural member and so that reflected ultrasonic pressure waves are transmitted to the acoustoelectric receivers or sensors on the panels.

Transducer elements 114 and 116 are operatively connected to a signal processor 120 which generates electrical a-c voltages of a number of different ultrasonic frequencies for energizing the ultrasonic pressure wave generators from among transducers 114 and/or 116. Signal processor 120 also analyzes incoming reflected ultrasonic pressure waves detected by the sensors or receivers from among transducers 114 and 116. One function of the wave analysis performed by processor 120 is to generate three-dimensional electronic models of structural irregularities internal to the structural member under investigation. The electronic models may be displayed on a monitor 122 for visual inspection by an operator. Alternatively or additionally, the electronic models may be evaluated automatically, for example, by pattern recognition techniques to determine whether the structural irregularities represent defects potentially leading to structural failure.

As further illustrated in FIG. 1, the integrity investigatory apparatus includes clamping or closure elements such as straps or bands 124 and 126 which may be locked in configurations of variable dimensions, for instance, by buckles 128 and 130. Straps or bands 124 and 126 surround panels 118 for purposes of limiting outward motion of those elements induced by pressurization of bag 104. In using the apparatus of FIG. 1, straps or bands 124 and 126 are initially loose or unfastened and bag is at least partially collapsed or deflated. Carrier 102 is maneuvered relative to a structural member such as girder or concrete beam 110 (FIG. 2) or a metal web such as an airplane wing 112 (FIG. 3) so that flexible web 108 faces and is in at least partial contact with an outer surface of the structural member and so that bag 108 is positioned between that outer surface and panels 118. Straps 124 and 126 are then manipulated to surround the positioned panels 118, bag 108 and the structural member, with buckles 128 and 130 being locked to fasten the straps. Fluid is then conveyed from source 106 into bag 104 to pressurize the bag and press flexible web 108 into conformation with the outer surface of the structural member, e.g., girder or concrete beam 110 (FIG. 2) or a metal web such as an airplane wing 112 (FIG. 3).

Panels 118, straps 124 and 126 and buckles 128 and 130 cofunction in part as an expansion restrictor surrounding bag 104 for limiting outward expansion thereof in a direction opposite the structural member under investigation. It will be readily appreciated that different methods of attachment may be used to fix the locations of panels 118, bag 104, and concomitantly transducers 114 and 116 relative to each other and relative to the structural member being scanned by the apparatus of FIG. 1. For example, panels 118 may be connected to one another by ratchet devices (not shown), bolts and brackets (not shown), hydraulic cylinders (not shown), etc.

FIG. 4 depicts functional components of processor 120, as well as a portion of flexible web 108 with an array of transducers 114. For purposes of explicating the structure and function of the integrity investigatory apparatus of FIG. 1, a portion of a panel 118 and transducers 116 may be alternatively depicted in FIG. 4.

Processor 120 includes an a-c current generator 132 producing alternating electrical waveforms in a plurality of separate frequency ranges. Pressure waveforms of different ultrasonic frequencies have different penetration depths and resolutions and provide enhanced amounts of information. Generator 132 is operatively connected to at least one of the electromechanical pressure-wave-generating transducer elements 114 and/or 116 for energizing that transducer element to transmit ultrasonic pressure waves into the structural member being subjected to a defect-seeking scanning operation. A switching circuit or multiplexer 134 is inserted at an output of generator 132 for connecting that unit to different wave generating transducers 114 or 116 in a predetermined or preprogrammed sequence. In addition, the frequencies of the energizing waveforms produced by generator 134 may be varied according to a pre-established program.

The piezoelectric receivers or sensors among transducers 114 or 116 are connected to a digital-to-analog converter 136 via another switching circuit or multiplexer 138 which links the different receivers or sensors to the converter in a predetermined or preprogrammed sequence determined by processor 120. Processor 120 may include a specially programmed digital computer 152 wherein functional modules, illustrated in part in FIG. 4, are realized as generic digital processor circuits operating pursuant to preprogrammed instructions.

Switching circuit or multiplexer 138 relays signals incoming from respective acoustoelectric receivers or sensors from among transducers 114 and/or 116 in a predetermined intercalated sequence to analog-to-digital converter 136, the output of which is stored in computer memory 140 by sampling circuit 142. A wave analysis module 144 retrieves the digital data from memory 140 and processes the data to determine three dimensional substructures or irregularities inside a structural member being ultrasonically scanned. This three-dimensional structural data may be provided to a view selection module 146 for deriving two-dimensional images for display on video monitor 122. In response to commands entered via a keyboard 158, view selection manipulates the electronic model or analog by conventional three-dimensional programming to rotate the defect about three Cartesian axes. A filter module 150 serves to remove selected substructures, for example, overlying structural irregularities already diagnosed as being innocuous, from the image presented on video monitor 148. Sampling circuit 142, wave analysis module 144, view selection module 146, and filter module 150 are program-modified generic digital circuits of computer 152.

Computer 152 contains additional functional modules, for example, a defect highlighter 154 and a superposition module 156. Filter module 150, defect highlighter 154 and superposition module 156 may be tied at respective inputs (not designated) to keyboard 158 or other operator interface device (such as a voice recognition component) for enabling an operator to delete substructures from the displayed image, to highlight or otherwise emphasize substructures in a displayed image, or to insert of words or other symbols on the image displayed on video monitor 148. More specifically, highlighter 154 operates to provide a different color or intensity or cross-hatching to different parts of an image to highlight a selected image feature, while words or symbols inserted by superposition module 156 may be a diagnosis or alert signal produced by a message generator module 160 of computer 152 in response to a diagnosis automatically performed by a determination module 162 of computer 152. Module 162 receives the processed image information from waveform analysis module 144 and consults an internal memory 164 in a comparison or pattern recognition procedure to determine whether any internal substructures of a structural member under investigation are a defect which might eventually result in a failure of the structural member. The detection of such a defect may be communicated to the operator by selectively removing overlying substructures, by highlighting defect features, or superimposing an alphanumeric message on the displayed image. Accordingly, message generator 160 may be connected to filter module 150 and defect highlighter 154, as well as to superposition module 156. The communication of an abnormal condition may be alternatively or additionally effectuated by printing a message via a printer 166 or producing an audible message via a speech synthesis circuit 168 and a speaker 170.

Filter stage 150 may also function to highlight selected structural irregularities internal to a structural member being investigated via an ultrasonic scanning procedure. The pattern recognition techniques referred to above may be used to detect structural defects having preselected characteristics. The highlighting may be implemented exemplarily through color, intensity, cross-hatching, or outlines.

As discussed above, the ultrasonically derived three-dimensional structural information from waveform analysis module 144 may be transmitted over a telecommunications link (not shown in FIG. 4) via a modulator 172 and a transmitter 174. The transmitted information may be processed at a remote location, either by an engineer technician or a computer, to generate a diagnosis. This diagnosis may be encoded in an electrical signal and transmitted from the remote location to a receiver 176. Receiver 176 is coupled with message generator module 160, which can communicate the diagnosis or other message as discussed above.

Computer 152 is connected at an output to a video signal generator 178 (which may be incorporated into the computer). Video signal generator 178 inserts horizontal and vertical synchs and transmits the video signal to video screen 122 for displaying an image of internal structural irregularities thereon.

Processor 120 may incorporate a control unit (not shown) operatively linked to switching circuit 134 for energizing the electromechanical pressure-wave-generating elements of transducers 114 or 116 in a predetermined sequence and to selectively couple the receivers or sensors of transducers 114 and 116 168 in a pre-established sequence to sampling circuit 142. The sequencing may depends on such parameters as the target investigation depth, the material or composition of the structural member, as well as the geometry of the structural member being investigated.

Processor 120 and particularly computer 152 include generic digital processing circuits modified by programming for executing the necessary routines of the various functional modules illustrated in FIG. 4. For example, waveform analysis module 144 is a generic digital processing circuit or group of circuits modified by programming for deriving a digital or electronic model of the structural defect from the analyzed ultrasonic pressure waves. Diagnosis determination module 162 examines the derived digital or electronic model to determine the nature of the defect and the likelihood that the defect will lead to more extensive cracking or tearing. This examination may include an "electronic dissection" of the detected defect, breaking the electronic model of the defect into parts, and characterizing the defects and its component parts according to conventional materials science categories. In addition, the examination performed by diagnosis determination module 162 may include automatically comparing the digital or electronic model with digital or electronic models of known structural defects stored in memory 164.

Processor 120, and more particularly wave analysis module 144, must be provided with data from which the relative positions of transducers 114 and/or 116 can be ascertained. This data may be generated by a separate system of position sensors (see discussion below with respect to FIGS. 11 et seq.) or from ultrasonic signals generated and sensed by the transducer elements themselves (see discussion below with respect to FIGS. 5–9).

The apparatus of FIGS. 1 and 4 is easily portable. Moreover, in testing a large structural member such as girder 110 (FIG. 2) or airplane wing 112 (FIG. 3), carrier member 102 is simply removed from one section of the structural member and reapplied to another section of the structural member until essentially the entire member has been examined.

Structural members such as girder 110 (FIG. 2) to be tested by the apparatus of FIGS. 1 and 4 each have several sides or outer surfaces extending at angles with respect to one another. Flexible surface or web 108 is conformed to the structural member by placing the web in engagement with at least two surfaces of the structural member extending at a substantial angle relative to one another. In this case, bag 104 is positioned adjacent to the two non-planar surfaces of the structural member and is held in that position by panels 118 and straps 124, 126. Ultrasonic waveforms produced by generator 132 and resulting in outgoing pressure waves of the same frequencies in the structural member may have a plurality of different ultrasonic frequency ranges. The different frequency ranges have different penetration characteristics, as well as different resolving powers. The use of different frequency ranges provides a greater amount of raw data for analysis and diagnosis of internal irregularities of structural members.

As illustrated in FIG. 5, another ultrasonic pressure wave generating and detecting system for undertaking structural integrity investigations comprises a flexible substrate or web 180 carrying a plurality of modular transducer packages 182 disposed in a substantially rectangular array. Each package 182 comprises a rigid substrate 184 to which is mounted a multiplicity of piezoelectric crystal transducer elements 186. Transducer elements 186 are all electromechanical and may be termed "electroacoustic" in the case of excitation or transmission of ultrasonic pulses and "acoustoelectric" in the case of reception or sensing of reflected ultrasonic pulses. Transducer packages 182 may be off-the-shelf hardware pieces each having several linear arrays of some two hundred piezoelectric crystal elements 186.

As discussed above, web 180 may be formed as a panel, wall or surface of a fluid-filled flexible bag 104 for enhancing ultrasonic coupling with a curved surface such as airplane wing 112 (FIG. 3) or multiple angled surfaces such as in girder 110 (FIG. 2). Other measures may be utilized for facilitating ultrasonic pressure wave transmission from and to the transducer elements 186 of the various modular transducer packages 182.

Generally, it is contemplated that the piezoelectric crystal elements 186 of any given package 182 are energized simultaneously in excitation and scanned simultaneously in reception. Thus, each transducer package 182 functions as a single aperture. The purpose of this technique is to enhance image resolution. Further enhancement is achieved by coherent aperture combining, discussed below.

Piezoelectric crystal elements 186 are energized by ultrasonic electrical excitation waveforms produced by a signal generator 188 in response to signals from an acquisition controller 190 (Data transmission paths are indicated in FIG. 5 by solid line arrows, while control signal links are indicated in dot-dash lines.) The excitation waveforms from signal generator 188 are directed to selected packages or apertures 182 by a switching circuit or multiplexer 192 in response to control signals from acquisition controller 190. The excitation waveforms are of variable frequency, determined on a continuing basis by acquisition controller 190 and more particularly by a frequency determination module 193 (FIG. 9) thereof, for optimizing image resolution at different depths (range) into the structural member to thereby obtain a uniform resolution along all coordinate axes. Generally, the higher the frequency, the greater the depth or penetration of effective data acquisition.

The excitation waveforms are generally transmitted in bursts, packets, or pulses of short duration. Any one packet or pulse may be directed to a single package or aperture 182 (single aperture excitation) or to multiple packages or apertures 182 simultaneously (multiple aperture excitation).

Multiplexer 192 is connected to a receiver 194 and is responsive to acquisition controller 190 for selectively connecting the transducer elements 186 of packages or apertures 182 to the receiver. Receiver 194 dynamically focuses incoming signals to produce a number of vectors (range lines) of image data. To that end, receiver 194 incorporates demodulation circuits (not separately shown) to obtain coherently the received signals. It is to be noted that multiplexer 192 may be disposed in whole or in part on web 180. Alternatively, the multiplexer may be located at a workstation.

Completely different packages or apertures 182 may be used for carrying out the excitation and reception phases of a data acquisition process. In an alternative operating mode, at least some of the excitation packages or apertures 182 are also be used for receiving reflected ultrasonic pressure waves from internal structures of a structural member during an ultrasonic scanning procedure. This operating mode is termed a "bistatic" or "multistatic" operating mode. In single-pulse bistatic or multistatic operation, a single transducer array or aperture 182 is energized by a single high frequency pulse, the same transducer array or aperture as well as one or more additional transducer arrays or apertures 182 being scanned to detect returning ultrasonic pulses. In two-pulse bistatic or multistatic operation, an excitation package or aperture 182 is energized sequentially with two excitation pulses of the same or different frequencies. Pressure waves reflected from internal microstructures in response to the first pulse are detected by one or more first transducer arrays or apertures 182, while pressure waves reflected from internal structures in response to the second pulse are detected by one or more second transducer arrays or apertures 182 different from the first transducer arrays or apertures. The transmitting or excitation aperture may be scanned to detect returning pressure waves in response to the first or the second excitation pulse.

In a monostatic operating mode, each transducer array or aperture 182 functions as the only receiver for ultrasonic pressure waves reflected from internal structural irregularities or potential structural defects in response to an excitation pulse produced by that transducer array or aperture. Simplistically described, in this operating mode a first pulse is transmitted and received by a first transducer array or aperture, while a second pulse is transmitted and received by a second transducer array or aperture. Thus, the same aperture is used for both transmission and reception. The monostatic operating mode has the disadvantage of possible phase shifts in data received by the second transducer array or aperture, as compared with data received by the first transducer array or aperture, due to a different substructure scattering geometry.

As discussed above, several packages or apertures 182 may be energized simultaneously with a single excitation pulse, while several packages or apertures 182 may be scanned at once to detect incoming pressure waves reflected from substructures of a structural member in response to the outgoing excitation pulse. This scanning process entails operation of a coherent aperture combining module 196 connected at a data input to receiver 194 and at an output to an image processor or higher-level wave analyzer 198.

Image processor 198 utilizes the increased resolution data from module 196 to construct three-dimensional models or analogs of internal structural irregularities of a structural member during a real time scanning operation. As discussed above with reference to other embodiments of an ultrasonic imaging system, an image is constructed by image processor 198 pursuant to instructions entered by a user via a keyboard 200 or other input device and received by a command and control unit 202. The constructed image is displayed on a monitor 204 by command and control unit 202.

During a structural integrity investigation utilizing the system of FIG. 5, a user may request an image of a particular region of a structural member via input device or keyboard 200. Command and control unit 202 interprets the request and relays the interpreted request to acquisition controller 190. Controller 190 queries image processor 198 to determine whether an image of the requested region is already stored in an internal memory (not shown) of the image processor. If the data is already obtained or is obtainable via interpolation, image processor 198 constructs the requested image, which is then passed to monitor 204 via command and control unit 202. If the data required for imaging the requested region of the structural member is not in memory, acquisition controller 190 determines which transducer packages or apertures 182 must be excited and which transducer apertures 182 must be scanned in order to obtain sufficiently high resolution data to form an image of the requested region of the structural member under investigation. Pursuant to its determination, acquisition controller 190 activates signal generator 188, multiplexer 192, and receiver 194 to implement the acquisition of the requisite data. Prior to data collection, acquisition controller 190 accesses a calibration unit 206 to determine whether a calibration sequence is needed. If so, acquisition controller 190 activates signal generator 188, multiplexer 192 and receiver 194 to conduct an ultrasonic scan for purposes of determining the locations and orientations of the various packages or apertures 182 relative to each other.

Calibration is effectuated by one or both of two techniques. The first technique utilizes acoustic point scatterers 208 (FIG. 6) such as AIUM phantoms disposed on packages or apertures 182. Basically, transducer packages or apertures 182 are activated under the control of acquisition controller 190 to obtain position data on the various point scatterers 208, while module 196 executes a self-cohering algorithm to determine the exact relative positions of the point scatterers, thereby determining the locations and orientations of substrates 184. It is contemplated that phantoms could be embedded in web 180 so that a sufficient number of point scatterers are always in the image field of the group of apertures requiring registration. The calibration data may be acquired bistatically (using a single pulse) or monostatically (using multiple pulses), as described above.

Figure 7:
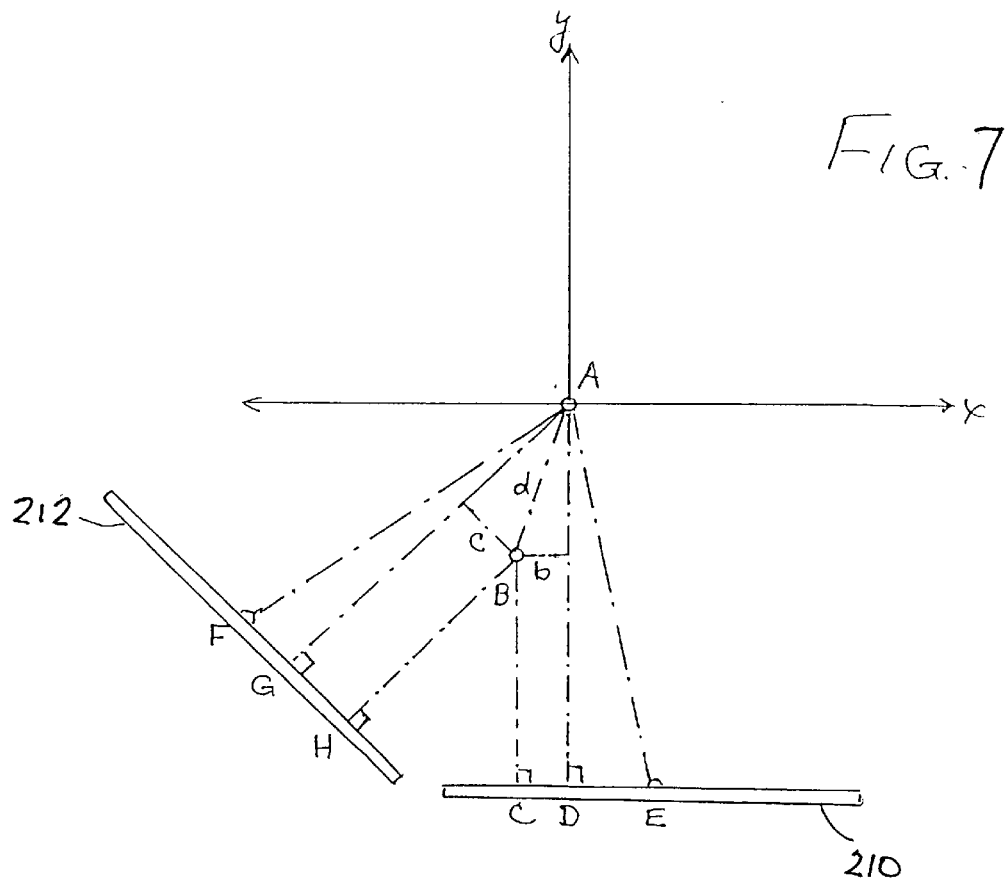
FIG. 7 is a diagram of two relative spaced and rotated modular transducer packages or array apertures similar to that of FIG. 6, showing geometric parameters in a calculation of relative position and orientation.

FIG. 7 is a diagram illustrating geometric parameters in the first calibration technique. Two point scatterers or AIUM phantoms are located at points A and B while transducer arrays or apertures 210 and 212 are centered at points E and F. Transducer array or aperture 212 is rotated through an angle EAF and translated a distance AF-AE from the position of transducer 210. To register transducer 212, it is necessary to determine angle EAF and distances AF and AE. Distances FG, FH, GA, and HB are measured from data produced by transducer array or aperture 212, while distances ED, EC, DA, and CB are measured using data generated via transducer array or aperture 210. Lengths b, c, and d are easily calculated next. Then, angle DAG is computed. Subsequently, angles EAD and GAF and lengths AE and AF are determined. Angle EAF equals angle EAD plus angle DAG plus angle GAF. ( EAF=EAD+DAG+GAF.) The key to these computations is to recognize that the length of the vector joining two point scatterers is invariant under coordinate system translations and rotations and hence will be measured the same from both transducer array or apertures 210 and 212.

Assuming significant signal-to-noise ratios, the cross-range measurements are as good as the apertures can provide, i.e., one picks the vector position where each point scatterer has maximum intensity. Azimuthal centroiding can be used to further improve the cross-range accuracy, depending on the size and orientation of the point scatterers relative to the cross-range resolution of the arrays. To obtain suitable coherent aperture combining results, the range measurements need to be accurate to the array focusing precision, which is better than 10 microns for premium systems. With sufficient signal-to-noise ratios, such accuracies can be achieved by range over sampling (i.e., using the highest A/D sampling rate available) combined with range centroiding techniques. In addition, the point scatterers could also be fabricated in pairs (or triplets, etc.) so that their separations are precisely known, which will assist in making the resulting positioning information more accurate.

Pursuant to the second calibration technique, a direct-path self-cohering algorithm is used. A calibration or reference array or aperture receives a pulsed signal from two or more arrays, whose positions and orientations are to calibrated relative to each other. The reference array is disposed generally on one side of a structural member while the arrays to be calibrated are disposed on another side of the body. In a given transverse plane through the structural member and a circumferentially extending array of transducer apertures 182, the locations of two points on each array are needed to position and orient the array. (In a more general procedure, the locations of three points on each transducer must be determined.) Solving for the position of a given point on a given array is a triangulation process using two half apertures of the reference array. The two points (or phase centers) on each array correspond to two sub-apertures with a high enough F# in azimuth and elevation to ensure that the calibration array is in the image field. Let each sub-aperture transmit a pulse (or two pulses in sequence if array element access is not available) and let the calibration array receive and process the pulse(s) in each of the two sub-apertures. By measuring the range difference between the two, the position of the array point can be computed relative to the reference array. It is to be noted that this description assumes that the reference array and the arrays to be calibrated are nominally in the same elevation plane. The process is repeated for all transducer arrays or apertures 182 that are to be positioned relative to each other. If all of the arrays in the plane are to be calibrated, then different arrays take turns being the calibration array. having multiple calibration arrays also allows estimate from different calibration arrays to be averaged, perhaps making the process more robust to deviations from planarity.

Accordingly, in the second calibration technique, the positions of a plurality of preselected individual transducer elements 186 are determined for each package or aperture 182 required to image the requested internal region of the structural member under investigation, thereby specifying the location and orientation of those requisite packages or apertures 182. The preselected individual transducer elements 186 are sequentially or separately energized with at least one packet or pulse of a predetermined frequency. At least one preselected transducer array, package or aperture 182 is then polled or sampled to sense incoming ultrasonic pressure waves of the predetermined frequency transmitted directly (unreflected, although perhaps refracted) through the internal structural irregularities or potential defects of the structural member. Of course, bistatic operation and access to individual transducer elements in an array are required for this calibration procedure to work. The array element access requirement could be eliminated by building reference arrays that consist of two elements joined rigidly (i.e., with known, fixed separation).

The calibration procedure may be performed at regular intervals, with a periodicity determined inter alia by such factors as the target region in the structural member, the purpose of the imaging process, and the processing capacity of image processor 198. Image data collection for a target region in or near the heart must be updated more frequency than image data collection for a target region in a quiescent limb. Generally, therapeutic invasions require continuous monitoring to a higher degree than diagnostic procedures. Of course, an image processor with a relatively low processing capacity will not be able to handle large data sampling rates.

It is to be noted that calibration may alternatively be effectuated by an auxiliary or external sensing system different from transducer arrays or apertures 182.

Coherent aperture combining as implemented by module 196 is an application of techniques known in the transmission and reception of wireless signals, including electromagnetic radiation of various frequencies, as in the field of astronomy. Antenna array principles are straightforwardly applied to an imaging system in order to improve the spatial resolution provided by extant ultrasound array apertures. In general, the larger the combined aperture, the better the lateral resolution.

The ultrasonic imaging systems disclosed herein include appropriate hardware and software (not illustrated) for signal amplification, analog-to-digital conversion, and focusing. The advantageousness of these functions, as well as the elements required to perform these functions, are well known in the conventional ultrasound arts and are not belabored herein.

Figure 8:
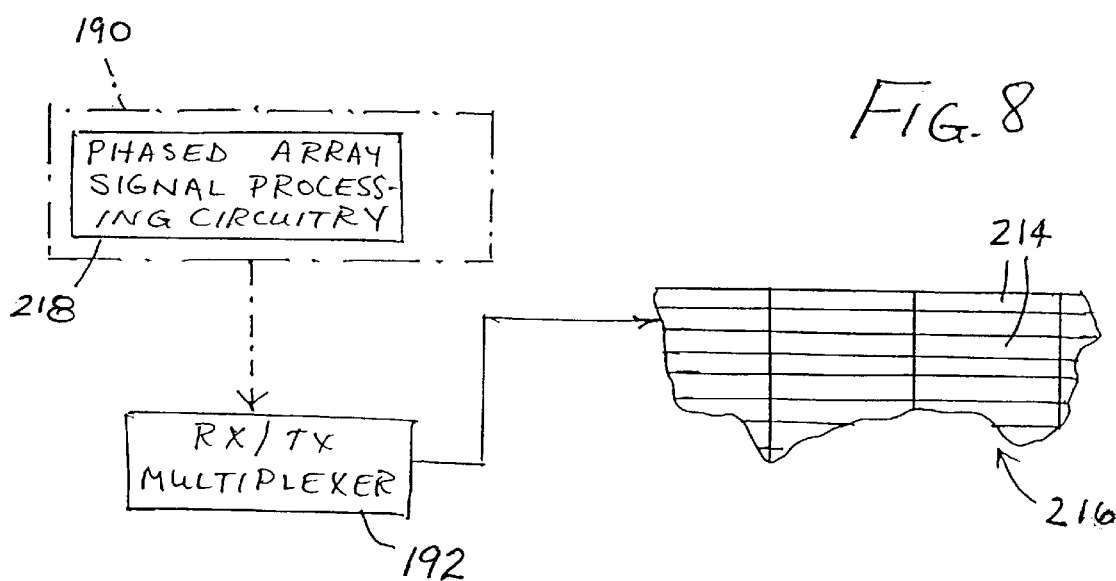
FIG. 8 is partially a schematic perspective view and partially a block diagram showing a modification of the ultrasonic imaging componentry of FIG. 5.

FIG. 8 depicts transducer hardware which can be disposed in or on panels 118 (FIG. 1). A multiplicity of off-the-shelf transducer packages or apertures 214 are rigidly connected to each other in a rectangular array to form an ultrasonic sensor platen 216. As described above with reference to FIG. 1, platen or transducer carrier 216 is provided with fluid-filled flexible bag 104 disposable in contact with the structural member under investigation for facilitating transmission of pressure waves into the structural member from transducer packages or apertures 214 and transmission of reflected pressure waves from the structural member to receiving transducer packages or apertures 214.

Array or platen 216 of transducer packages or apertures 214 contains piezoelectric crystal elements (not shown) which are tightly packed along the lengths of the respective transducer packages or apertures 214 and which are sparsely packed along the widths of the respective transducer packages or apertures 214. In order to obtain a uniform resolution in both azimuthal and elevational directions, acquisition controller 190 (FIG. 5) is provided with phased-array signal processing circuitry 218 for effectuating a sweeping type scan of the internal structures.

Figure 9:
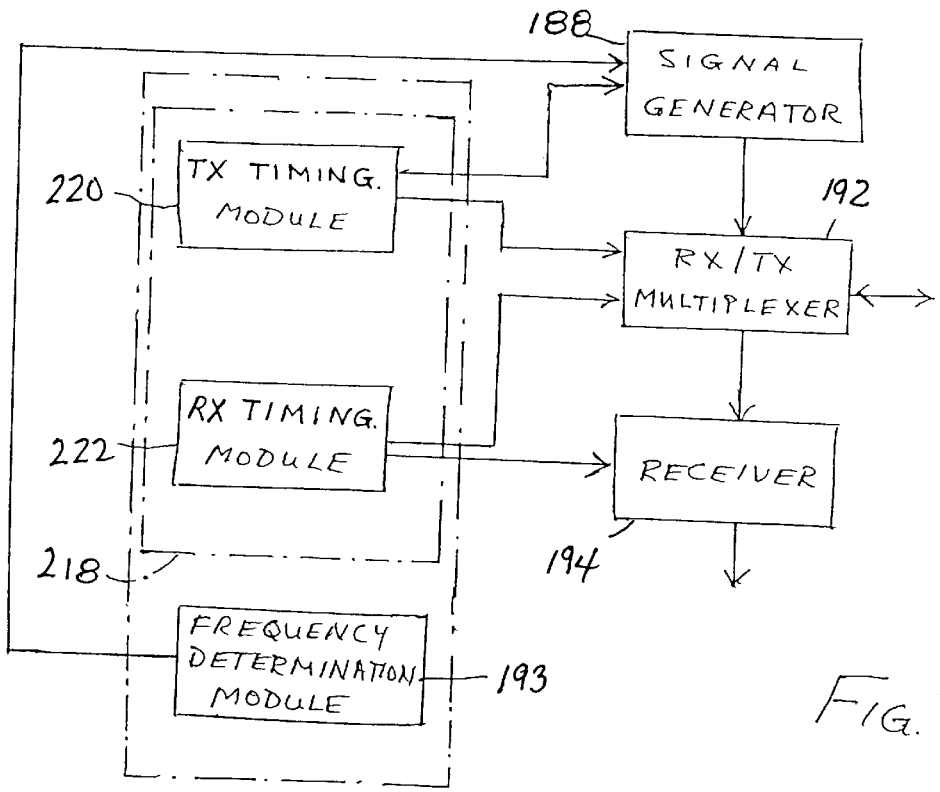
FIG. 9 is a block diagram of components of a phased-array signal processing circuit shown in FIG. 8, also showing components from FIG. 5.

As illustrated in FIG. 9, phased-array signal processing circuitry 218 includes a delay module 220 operatively connected to signal generator 188 and to multiplexer or switching circuit 192 for varying a phase of electrical signals sent to the different transducer packages or apertures 214 to effectuate a sweeping scan of internal irregularities or potential defects of a structural member by outgoing pressure waves. Thus, the variations in the phase of electrical signals sent to the different transducer packages or apertures 214 is effectuated in part by multiplexer or switching circuitry 192 under the control of acquisition controller 190 and more particularly in response to control signals from module 220 of phased-array signal processing circuitry 218.

As further illustrated in FIG. 9, phased-array signal processing circuitry 218 further includes a timing module 222 operatively connected to multiplexer 192 and receiver 194 for varying sampling times of transducer packages or apertures 214 to effectuate a staggered or sequenced scanning of incoming reflected pressure waves by transducer packages or apertures 214.

Phased-array signal processing circuitry 218, like acquisition controller 190 as a whole and other components shown in FIG. 5, is realizable in the form of generic digital processor circuits modified by programming to operate transducer packages or apertures 214 at least in one dimension (elevation or azimuth) as a phased array. Thus, phased-array signal processing circuitry 218 and the signal processing and control elements of FIG. 5 are all realizable by a properly programmed digital computer.

Of course, the physics of ultrasound are well documented and understood. Software for any of the ultrasonic imaging systems herein entails a straightforward application of the appropriate wave equations. See, for instance, *Principles of Aperture and Array System Design*, B. D. Steinberg, John Wiley, 1976, and *Ultrasonic Imaging Using Arrays*, Proc. IEEE, Vol. 67, No. 4, Apr. 1979, pp 484–495.

It is of interest that imaging occurs in the far field of each individual transducer element 186 and in the near field of package or array aperture 182. The near-field variation of a wavefront across an aperture 186 is quadratic. As a result, focusing an array aperture in a phased-array process is achieved by computing and applying the appropriate quadratic time delays, for the location in question that is being focused.

Figure 10:
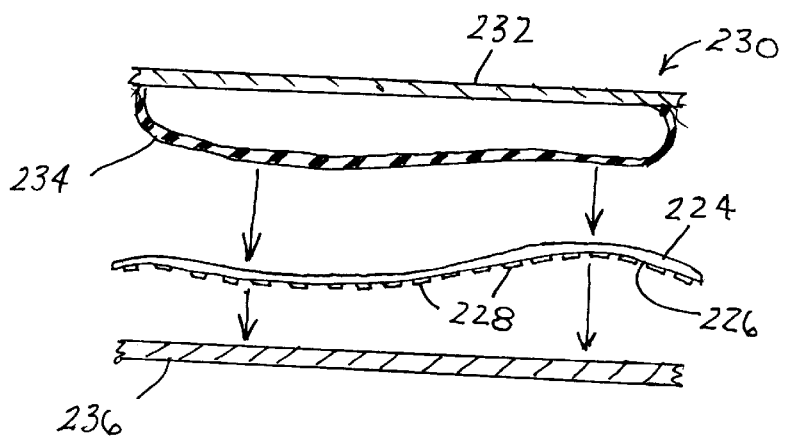
FIG. 10 is a schematic cross-sectional view of a pair of components of a modified system or apparatus for carrying out structural integrity investigations in accordance with the present invention.

As illustrated in FIG. 10, a flexible web 224 having a surface 226 on which are disposed a plurality of piezoelectric acoustic transducer elements 228 may be separate from a pressure application assembly 230 which includes one or more rigid panels 232 and a sack or bag 234 pressurizable with liquid for pressing web 224 and particularly transducer elements 228 against a structural member 236 under investigation.

Where rigid panels 118 (FIG. 1) are provided with ultrasonically excitable transmitting and receiving transducer elements 116 for use in a structural integrity investigations, the relative positions of the transducer elements 116 may be determined by ascertaining the positions and orientations of panels 118 with respect to one another, given that the (fixed) positions of the transducers elements on the respective panels are known. Various methods of determining the relative positions of rigid plate shape elemetns such as panels 118 are discussed below. Determining the relative positions of transducer elements 114, which must be done each time the apparatus of FIG. 1 is reconfigured in a new position on a structural member, may be implemented by the signal analyzing techniques described hereinabove. Alternatively, the complex shape of the web 108 may be determined, for instance, by internal strain gauge measurements and other techniques, described below. Initially, a calibration procedure is described is described with reference to FIGS. 11, 12A and 12B.

Figure 11:
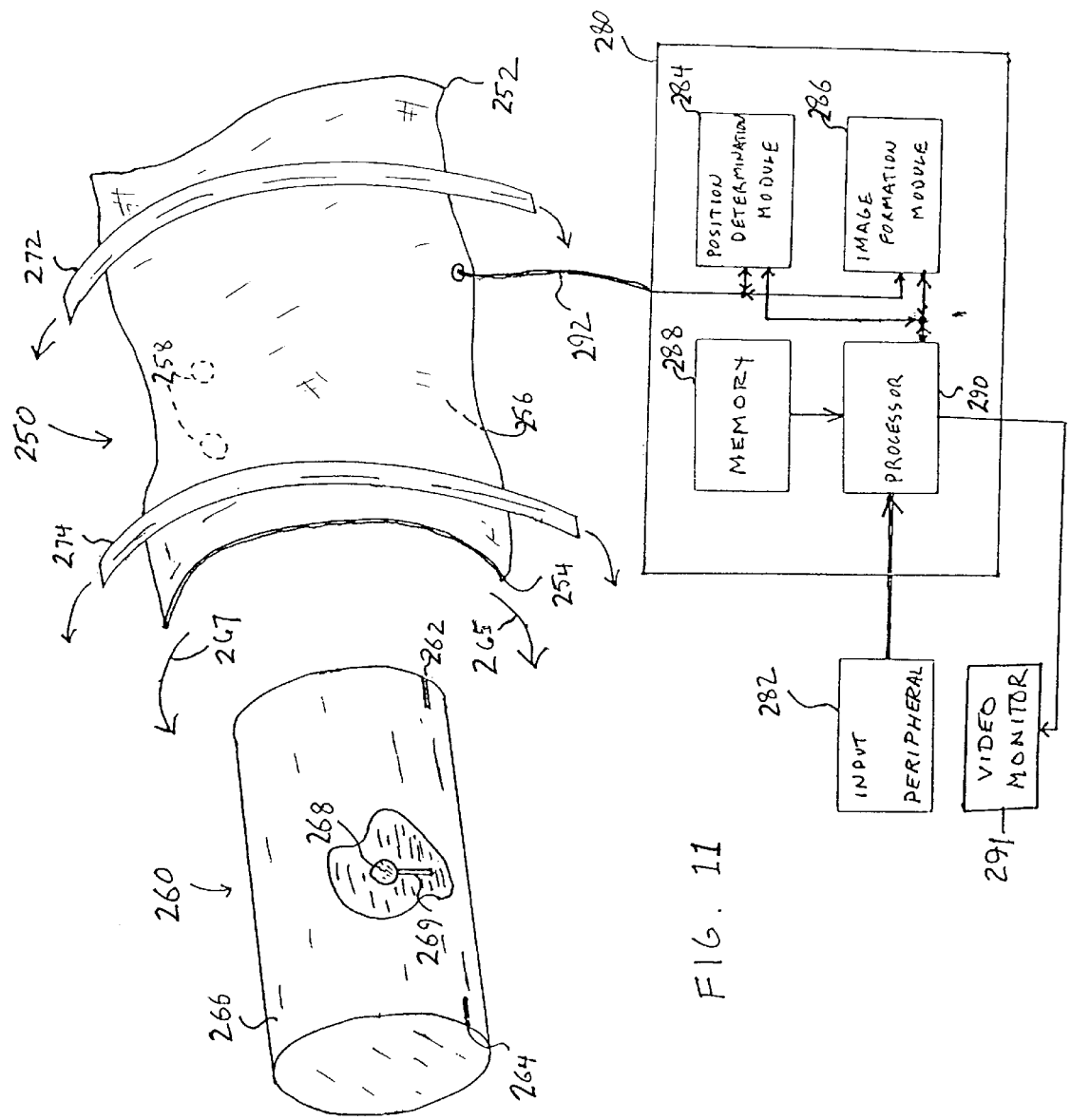
FIG. 11 is partially a perspective view and partially a functional block diagram of an acoustic imaging device and components for calibrating the device.

A method of calibrating an acoustic imaging device in the form of a web 250 with a plurality of attached acoustic transducers 258 is outlined in FIG. 11. Transducers 250 are generally piezoelectric crystal elements capable of sonic and ultrasonic signal conversion. Flexible substrate or carrier web 250, operationally connected to a control system 280 via an umbilical 292, is wrapped around a standard calibrating body 260, in this instance a solid cylinder. Comers 252, 254 of web 250 are aligned with fiducial marks 262, 264 respectively and the web is pulled taut so that an inner surface 256 of the web is disposed securely in contact with an outer shell 266 of cylinder 260, an operation suggested by solid arrows 265 and 267. Active faces of transducers 258 are disposed on inner surface 256. Cylinder 260 contains a fluid (not designated), such as water, gel, or a water-gel mixture, possessing adequate acoustic transmissibility for a range of frequencies utilized by the imaging device. Cylinder 260 also contains a target body 268 of known dimensions and shape mounted on a support 269 in a predetermined location. The target body thereby has a fixed geometric relation to the fiducial marks 252, 254. Web 250 may be secured around cylinder 260 by mechanical fasteners integral to the cylinder and web (not illustrated) or by straps 272, 274. A calibration operation begins by executing a command delivered via an input peripheral 282 to control system 280. A selection of a calibrating body from among several standard bodies may also be fed to control system 280 by an operator via input peripheral 282. Standard calibrating bodies vary in geometry of the shell, geometry of the internal target, and identity of the fluid. Information concerning standard calibrating bodies may be stored in a memory 288 and automatically accessed during a calibration procedure following input of body selection by an operator. While a simple cylinder ontaining a single internal target is adequate for routine system calibration, more complex calibrating bodies or a series thereof may be utilized in factory calibration or following major maintenance.

Figure 12A:
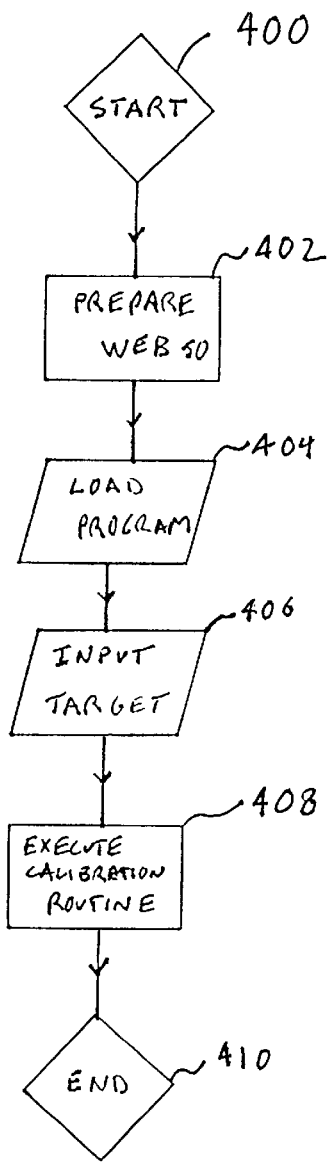
FIG. 12A is a flow chart of a method for calibrating an acoustic imaging device, depicting operator steps.
Figure 12B:
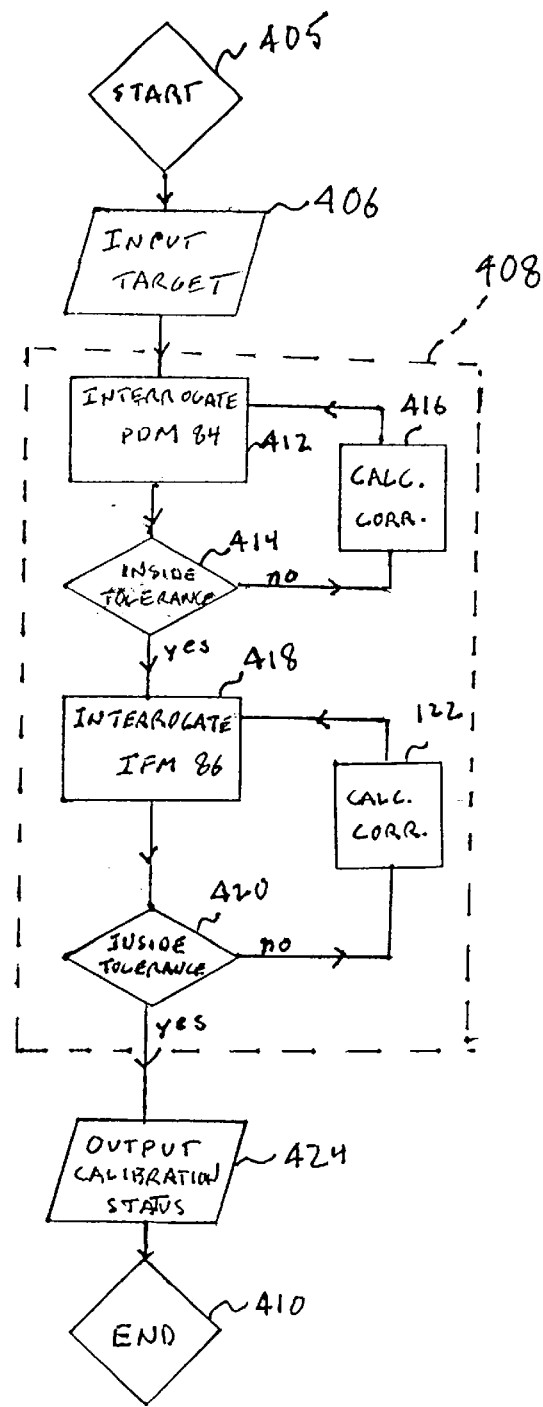
FIG. 12B is a flow chart of a method for calibrating an acoustic imaging device, depicting machine steps.

Memory 288 also contains in a machine readable format at least one calibration program for execution by a processor 290 of control system 280. A flowchart of operator executed steps in a calibration procedure is shown in FIG. 12A, and a flowchart of machine executed steps in the calibration procedure is shown in FIG. 12B. In an overall operator executed process (FIG. 12A), a logical start 400 is followed by mounting of web 250 on calibrating body 260 in step 402. In step 404 a calibration program located in memory 288 is loaded into processor 290 and begins execution. The operator is prompted to input the standard target body selected from a list of standard target bodies in step 406, following which input a machine calibration routine 408 is executed by processor 290 in cooperation with Position Determination Module (PDM) 284 and Image Formation Module (IFM) 286. Completion of the overall procedure is denoted by logical end step 410. The calibration routine of step 408 is shown in greater detail in FIG. 12B.

Following a logical start 405, the program commences execution by prompting a user for input in step 406. After a user response in step 406, program execution continues in step or subroutine 412 which includes an interrogation of position determination module (PDM) 284. The PDM returns putative positions of transducers 258 attached to web 250, based on outputs of position determination means to be described hereafter. Following completion of step or subroutine 412, a comparison step or test 414 determines whether putative positions of transducers 258 are within a pre-established tolerance of transducer reference positions associated with the standard calibrating body downloaded from storage means 288. In case the putative positions are out of tolerance, one or more corrective coefficients or settings are generated by processor 290 in a step 416, and used as an input to the PDM in a subsequent iteration of step 412. Steps 412, 414, 416 are repeated sequentially until a satisfactory result or exit status of test 414. Following a satisfactory exit status of test 414, program execution continues in a subroutine or step 418 which includes an interrogation of image formation module (IFM) 286. The IFM returns a putative geometry or model of target body 268, including a relation to outer shell 266 of standard calibrating body 260. Following completion of step or subroutine 418, a comparison step or test 420 determines whether putative geometry of target 268 is within a pre-established tolerance of a target reference geometry downloaded from storage means 288. In case the putative target geometry is out of tolerance as determined directly by sensing of relative positions or indirectly through interpolation, one or more corrective coefficients or settings are generated by processor 290 in a step 422, and used as an input to the IFM in a subsequent iteration of step 418. Steps 418, 420, 422 are repeated sequentially until a satisfactory result or exit status of test 420. Following a satisfactory exit status of step 420, a calibration status is displayed to the operator in step 424, which is followed by logical end 410 to both machine executed and operator executed steps in the overall calibration procedure.

Standard calibrating bodies containing more complex internal targets (not shown) than simple sphere 268 and post 269 are used for more comprehensive adjustment and compensation in a lengthier calibration procedure.

It is to be understood that position determination module 284 and image formation module 286 may be realized by specialized or hard-wired electronic circuitry, or by programming of generic digital components of processor 290, or a combination of these approaches, and that corrective coefficients or settings generated by sub-procedures 412, 414 may be stored by physical means associated with modules 284, 286, such as specialized non-volatile memory registers, or generically by memory 288 which may be an internal memory area of processor 290. The above description of a calibration procedure is accordingly in no way meant to limit possible physical realizations of functional components of control system 280.

Processor 290 obtains acoustic data from transducers 258 and cooperates with position determination module 284 to generate a virtual image or electronic model of internal structural irregularities and potential structural defects of a structural member on which web 250 is placed. The activation of transducers 258 to generate ultrasonic pressure waves transmitted into the structural member and the receiving and processing of reflected ultrasonic pressure waves received by the transducers is described in U.S. Pat. Nos. 5,666,953 and 5,871,446 for an ultrasonic medical imaging system. The disclosures of those references are incorporated by reference herein. The present discussion with reference to FIGS. 11 through 26A is largely concerned with providing an ancillary position sensing and determination system for ascertaining the locations of transducers 114 or 116 relative to one another. As described above with reference to processor 120 (FIGS. 1 and 4), processor 290 derives two-dimensional images from the virtual image or electronic model of the internal structures and transmits those images in video signal form to a video monitor 291 for display to an operator. Processor 290 cooperates with image formation module 286 to generate the images for display on monitor 291.

In one calibration procedure utilizing the apparatus of FIG. 11, transducers 258 are operated, after the placement of carrier web 250 onto calibration cylinder 260, to transmit ultrasonic pressure waves from the transducers into cylinder 260. Pressure waves reflected from target 268 are sensed by transducers 258 and processed by processor 290 to generate a virtual image or electronic model of target 268. Processor 290 accesses memory 288 and compares the constructed virtual image or electronic model of target 268 with an electronic duplicate thereof stored in memory 288. In response to this comparison, processor 290 cooperates with position determination module 284 to determine initial or reference positions of transducers 258 relative to one another. After this calibration procedure, carrier web or substrate 250 is removed from cylinder 260 and placed on a structural member. During the transfer of web 250, position determination module 284 constantly monitors changes in positions of transducers 258 relative to one another, whereby processor 290 is apprised of the instantaneous positions of transducers 258 relative to one another. This information is used by processor 290 in generating the virtual image or electronic model of internal structures of a load-bearing member on which web 250 is placed.

Figure 13:
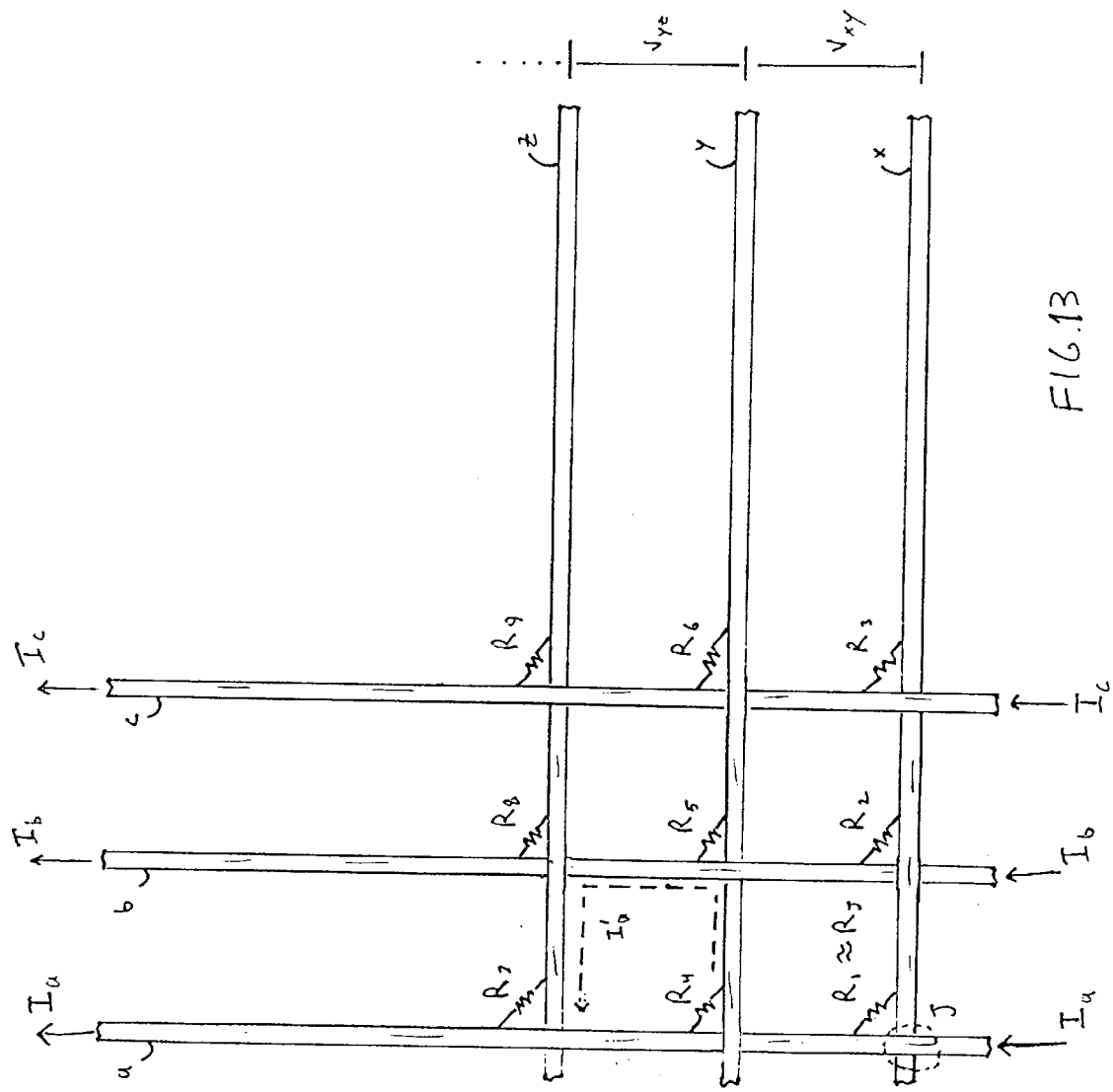
FIG. 13 is a partial schematic diagram of a system of continuous strain gauges utilizable as a sensor position determination system in an acoustic imaging device.
Figure 13B:
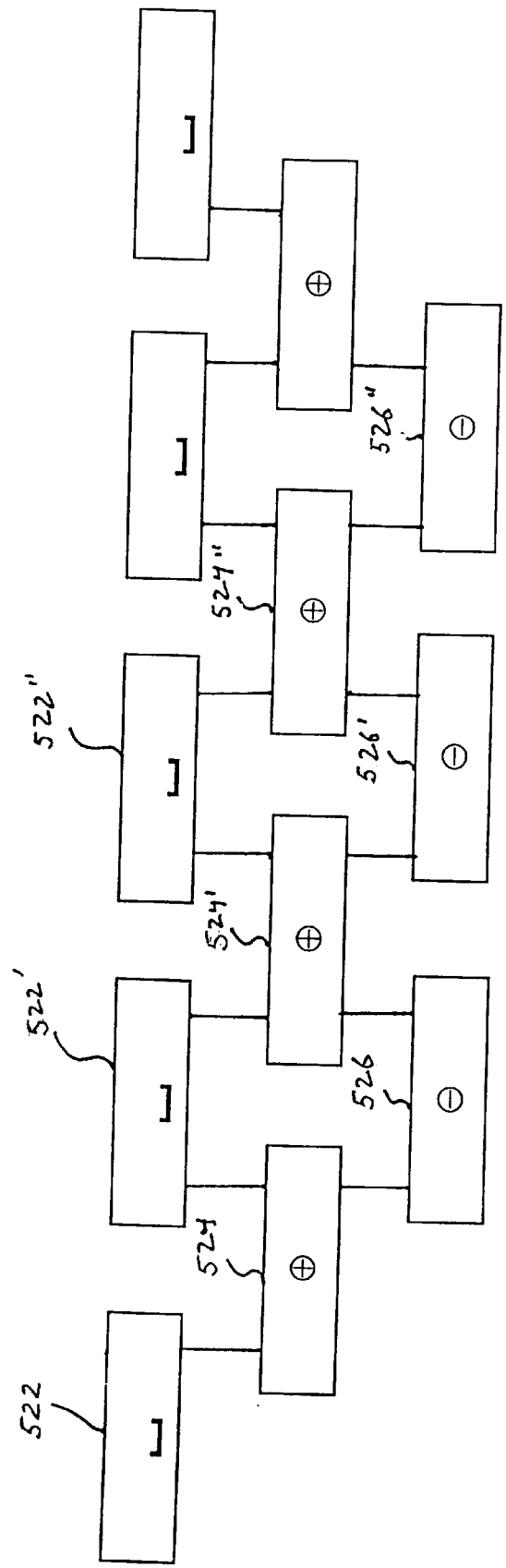

A method and device for internal determination of a strain state or configuration of a web or essentially two-dimensional flexible structure is schematically represented in FIG. 13. A dense network of strain-sensitive conductive ribbons or strips is woven into the web, as shown in FIG. 13 by representative vertical ribbons or warp strips a, b, c and horizontal ribbons or woof strips x, y, z. Warp strips are generally disposed in a first orientation or parallel to a first axis, and woof strips disposed in a second orientation or parallel to a second axis. The first and second orientations are preferably substantially perpendicular to one another. Resistance per unit length of the conductive strips is a function of a local strain state and hence a local radius and sense of curvature of the strips in a plane perpendicular to the drawing. Strain sensitive resistance may be realized, for example, by deposition of a thin metallic film on a flexible plastic substrate. Adjacent warp strips and woof strips are respectively substantially electrically isolated from strips of the same orientation, and make contact with strips of the other orientation at relatively high resistance joints, represented by generic joint J with nominal resistance R; actual joint resistances are represented by $R_1$–$R_9$. In a complete determination of strain state or configuration in a flexible two-dimensional structure according to the embodiment of FIG. 13, a first series of currents $I_a$, $I_b$, $I_c$, . . . is passed sequentially through respective warp strips. Because of position dependent strain sensitive conductance of strip a, varying potential differences $V_{xy}$, $V_{yz}$ are realized between junctions of equidistant warp strip pairs x, y and y, z associated with passage of current $I_a$ through strip a. Nominal or design joint resistance $R_j$ is chosen sufficiently high so that alternative path current flows, represented generically by current $I_a'$, are negligible in comparison to current $I_a$. High resistance joints may be achieved for example via deposition of a thin film semi-conductor on top of a thin film conductor, by formation of a durable metallic oxide layer, or by use of a semi-conductive cement.

During current excitation of strip a by current $I_a$, potential differences $V_{xy}$, $V_{yz}$, etc. are read from terminations of the woof strips x, y, z, . . . in multiplexed blocks determined by a physical wiring configuration of the web and associated processor 90 (FIG. 11). Each strip a, b, c, . . . x, y, z, . . . must be independently addressable. Strips in a first orientation, i.e. warp strips a, b, c, . . . are current excited sequentially until exhaustion, whereupon strips in a second orientation, i.e. woof strips x, y, z, . . . are sequentially current excited.

In this manner a complete strain state picture or configuration is built up, with potential difference measurements between adjacent pairs of strips in the first orientation and pairs of strips in the second orientation yielding a measure of surface curvature.

An alternative scheme of a continuous internal position monitoring system via strain or local curvature measurements is schematically illustrated in FIG. 14. A first set of conductors in a first orientation, represented by leads d, e f, a further set of conductors in a second orientation, represented by leads u, v, w, in addition to a second set of conductors underlying d, e, f in the first orientation, represented by d', e', f', function only as conductive leads rather than strain gauges. A strain gauge or deformation sensitive resistive element G, G' located at each intersection K between a lead of the first orientation and a lead of the second orientation and also at each intersection K' of a lead of the second orientation and a lead of the second set of leads of the first orientation, is conductively fixed to the respective leads. Strain gauges G, G' have a nominal or design resistance $R_G$. There is no direct conductive path between leads u, v, w and d, e, f or d', e', f' at intersections K, K'. A current $I_{dv}$ passing between termini of leads d, v, partially follows a main path P though strain gauge or deformation sensitive element G, associated with a potential difference or drop $V_G$ and a partial current $I_G$. Potential drop $V_G$ is substantially equal to a total potential drop V across the termini of leads d and v. Contributions of alternative current paths involve increasing numbers of resistive elements with an increasing remove from intersection K, as seen by a path p taken by partial current $I_{dv}^*$ but are not completely negligible. The relation of potential drop V to total current $I_{dv}$ over leads d, v is thus a measure of an average local strain state in a neighborhood of element G, with a maximum weighting on element G itself. A complete strain or configuration determination involves sequentially passing total currents $I_d = I_{du} + I_{dv} + I_{dw} + \ldots, I_e = I_{eu} + I_{ev} + I_{ew} + \ldots$, etc. through leads d, e . . . , d', e', . . . , clamping a single lead d, e, f, . . . of a first orientation and a block of leads u, v, w, . . . of a second orientation at a potential difference V, simultaneously measuring partial currents $I_{du}, I_{dv}, \ldots$ at leads u, v, . . . . Block size is determined by a physical wiring configuration of the web and of associated processor. An increase in geometrical resolution of strain measurement may be obtained at the expense of greater processing power by employment of mathematical inversion to extract a value of $V_G$ from a complete output $I_{du}, I_{dv}, I_{dw}, \ldots, I_{eu}, I_{ev}, I_{ew}, \ldots$ of a configuration determination. The form of a generic resistance as a nominal value $R_G$ plus a perturbation, along with diminishing importance of elements further removed from G in determination of $R_G$, may be exploited by those skilled in the mathematical arts to conduct the inversion with maximal computational efficiency. It is also to be understood in this embodiment that strain gauges G, G' et alia may be formed by continuously woven strips in the manner of the embodiment of FIG. 13, interwoven at a bias with respect to leads d, e, f, . . . u, v, w, . . . , it being advantageous in the case of gauges of higher intrinsic resistance to utilize a separate grid of conductive leads.

The previous two embodiments relate to a relatively dense point-to-point determination of a state of curvature or strain in a substantially two dimensional body. An alternative method of determining relative positions of multiple acoustic transducers disposed in multiple mountings measures a sufficient number of degrees of freedom between pairs of adjacent mountings considered as rigid bodies. Mechanical or other encoding means may be used to measure translation and rotation between adjacent mountings. Such a method advantageously exploits a mechanical reduction in total degrees of freedom.

A mechanical coupling and encoding device for rigid tiles or mountings is illustrated in FIG. 15A. Tiles 430, 430' are attached to flexible substrate 432. A mechanical measurement linkage between tiles 430, 430' comprises chiefly a first pivotal coupling 434, a second pivotal coupling 436, and a connecting rod 438. Couplings 434, 436 and rod 438 together permit a pitch or depression movement of tile and a roll or torsion movement of tile 430' with respect to tile 430, as indicated by double headed arrows aa and bb respectively. Couplings 434, 436 also include digital encoders (not shown) for producing a digital output signal representing a depression angle α (FIG. 15B) and torsion angle β (FIG. 15C), the signals being transmitted via a bus 440. In the embodiment of FIG. 15A, the mechanical linkage both constrains a number of degrees of freedom between adjacent tiles and incorporates measurement components for the remaining degrees of freedom. Other mechanical linkages enabling a larger number of degrees of freedom, up to an including a complete six degrees, may be contemplated.

Figure 17:
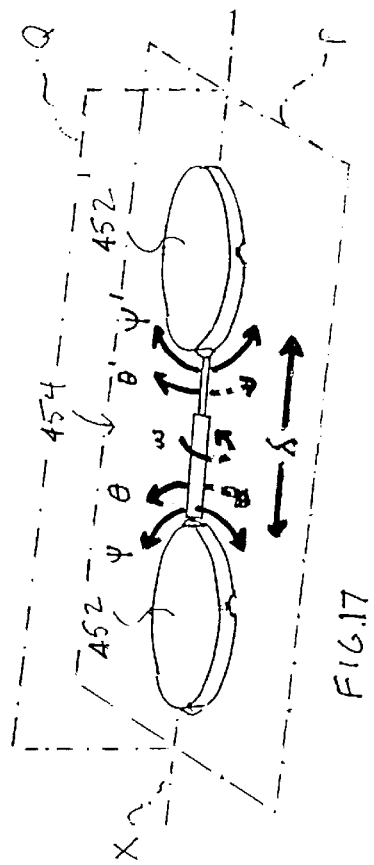
FIG. 17 is partially a perspective detail and partially a diagram showing a definition of angles in connection with a single linkage of the mechanical armature of FIG. 16.
Figure 16:
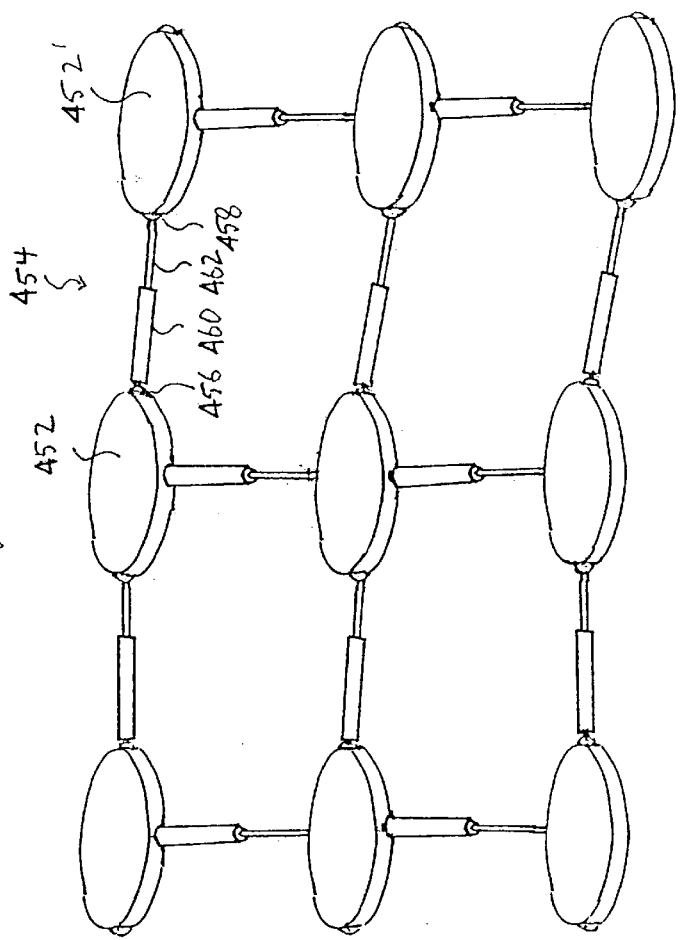
FIG. 16 is a perspective diagram of a mechanical armature utilizable as a sensor position determination system in an acoustic imaging system.

FIG. 16 depicts a mechanical linkage measuring up to six degrees of freedom between adjacent rigid plates or tiles 452. Plates 452 are connected to each other by arms 454 . A generic arm 454 comprises a piston 462 and a cylinder 460 assembled so as to allow extensible movement of piston 462 relative to cylinder 460. Ball and socket joints 456, 458 attach cylinder and piston respectively to adjacent plates 452, 452'. Realization of six degrees of freedom between adjacent plates via arm 454 is illustrated in FIG. 17. Plate 452 is free to rotate with respect to arm 454 in a substantially horizontal plane P through an angle ψ, and in a substantially vertical plane Q through an angle θ. Plate 452' is similarly free to rotate through angles ψ', θ in planes P, Q respectively. Plates 452, 452' are also free to rotate about a major axis X or arm 454 through an angle ω. Finally, a sixth degree of freedom is realized by an extension λ of arm 454. Laser interferometric methods, discussed below with reference to FIGS. 21 and 24 may be used by those skilled in the art to measure extension, and, by selection of appropriate beam paths, rotation.

An alternative mechanical linkage incorporating an intermediate number of degrees of reedom is illustrated in FIGS. 18 and 19. An extensible arm 470 is comprised of sliding sections 472, 474 with a substantially rectangular profile, not permitting rotation about a major axis of the arm. Arm 470 is affixed to an adjacent pair of disks or rigid mountings 480, 482, lying substantially in a horizontal plane, via brackets 476, 478 permitting rotation of the arm relative to disks 480, 482 in a substantially vertical plane. It will be perceived by a close consideration of a total assembly shown in FIG. 19 in conjunction with details of affixation shown in FIG. 18 that this alternative mechanical linkage allows at least one point on each disk 480, 482, etc. to conform to an arbitrary complexly curved surface within a range of local radii of curvature determined by dimensions of the arms and disks. An arbitrary orientation of a particular disk may not be further specified, however. Acoustic transducers (not shown) may be mounted directly on disks or plates 480. To facilitate ease of use, e.g., to prevent entanglement with other tools, a flexible web may cover the mechanical linkage of FIG. 19 excepting possibly the transducers.

A further modification of a transducer carrier conformable to a complex or curved structural member such as girder 110 or airplane wing 112, which permits a complete accommodation of an orientation of individual mounting plates to the structural member or other acoustic body, is illustrated in FIG. 20. Plate 480 is affixed to a ball 496 or a socket 494 of a universal joint 492. A secondary mounting plate 498 is affixed to the socket 494 or the ball 496 of joint 492, and enjoys at least two rotational degrees of freedom relative to plate 480. Measurement of an angular position of joint 492 may again be accomplished by laser interferometric methods, which will now be discussed in detail.

Figure 23A:
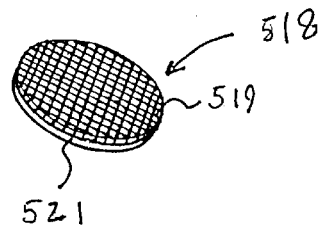
FIG. 23A is a schematic perspective of a chip-level logic sensor/fringe-counter.
Figure 23:
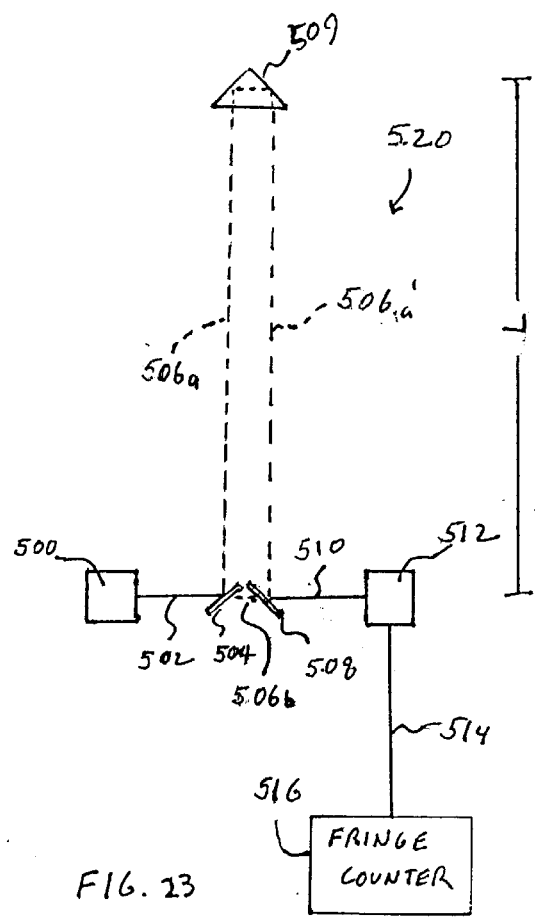
FIG. 23 is partially a schematic and partially a block functional diagram illustrating a laser interferometer utilizable as a sensor position determination system in an acoustic imaging device.

A laser interferometric distance measurement device useful in determining relative positions and orientations of rigid bodies such as panels 118 (FIG. 1) is illustrated in FIG. 23. A laser diode 500 projects a coherent monochromatic light beam 502 incident to a first beam splitter 504, where the beam is divided into partial beams 506a, 506b. Partial beam 506a is reflected by a prism 509 and returns as reflected beam 506a', which is recombined with partial beam 506b at a second beam splitter 508 to form a recombined beam 510. Beam 510 is incident on a photodetector 512, which contains a linear sensor array (not shown) for detecting an intensity of the recombined beam as varying over a range of a single dimension. The intensity of recombined beam 510 at a center of the range varies from a maximum when a path length difference between partial beams 506a, 506a' and 506b is an integral number of wavelengths to a minimum when the path length difference is a half-integral number of wavelengths. In addition, a fringe pattern, or pattern of maxima and minima, will move across the linear sensor array in either a right hand or left hand sense depending on whether a distance L between beam splitter 504 (or 508) and prism 509 is increasing or decreasing. An output of photodetector 512 is input to a fringe counter 516 via a connector 514. A logic unit (not shown) in fringe counter 516 combines a number of maxima incident on photodetector 512 with a sense of movement of the fringe pattern to track an instantaneous value of distance L, based on an increment to a preliminary value of L, $L_0$, established by some other means; for example, the calibration apparatus of FIG. 11.

Overall efficiency of a fringe-counting process, as described above, may be improved by incorporating chip-level logic into a fringe-counter, or sensor array, module 516, as illustrated in FIG. 23A. In analogy with preprocessing arrangements realized in ganglia backing the human eye, a substantial amount of central pixel-level processing may be avoided in machine-vision applications by use of chip or sensor level logic. Operations like fringe or edge recognition and movement detection may be carried out by means of a small number of nearest neighbor calculations, as is illustrated schematically in FIG. 23B.

Individual pixel receptors, symbolically represented by elements 522, 522', 522" et al. are linked in nearest neighbor pairs by arithmetic units or adders 524, 524', 524". The adders are further linked by a second level of logic represented by difference modules 526, 526', 526". The calculational scheme of FIG. 23B is schematic, and is meant to exemplify a general strategy of visual data processing rather than represent a particular definite algorithm. Conceptually, a first order pre-processing layer is represented by units 522 et alia, a second order pre-processing layer by modules or units 526 et alia; third order (not shown) and higher pre-processing layers are possible. Each layer arithmetically combines and reduces data from progressively more distant neighboring pixels, and may perform such data combination at a pixel or sensor refresh rate, thereby reducing a data processing load on a central processor and allowing visual data reduction in real time. In particular, algorithmic steps in edge detection, important for fringe counting in the current application, can be front loaded. Pre-processing layers situated directly adjacent to solid state sensor elements on a physical chip level may take advantage of relatively faster analog differencing, entailing charge shifted level comparing, and a subsequent digitization step is thereby executed on a smaller, partially processed, data set.

Solid state logic for performing pre-processing calculations may either be grown in situ behind a sensor array as part of a single, monolith solid state silicon device, or alternatively, distinct integrated circuits may be "bump bonded" to form a tightly integrated whole, as shown schematically by a logic wafer 521 bonded to optical sensor array 519 in FIG. 23A.

Figure 24:
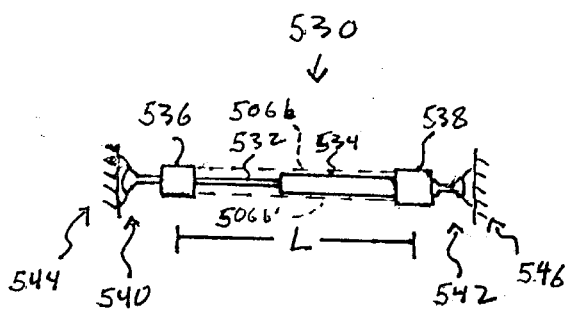
FIG. 24 is a detail of a single mechanical linkage equivalent to those of FIG. 16, showing a mode of utilizing a laser interferometer in accordance with FIG. 23.

A length measuring laser-interferometric assembly 530 is illustrated in FIG. 24. An extensible assembly comprises a pair of rigid members 532, 534 slidably coupled to one another connected via ball-and-socket joints 540, 542 to respective transducer carriers or substrate bodies 544, 546. Electro-optical sub-units 536, 538 are mounted on members 532, 534 respectively. Sub-unit 536 contains diode 500 (FIG. 23) and photodetector 512, while sub-unit 538 contains prism 509. Partial beam paths 506b, 506b' pass between the subunits, and members 532, 534 serve to maintain a sufficiently straight optical path between units to insure partial beam incidence on beam splitters 504, 508 and prism 509. Assembly 530 permits a range of motion over a full six degrees of freedom between bodies 544 and 546, of which one, a length or extension L, is measured. Effectively, an extension is measured between fixed points in relation to bodies 544, 546 represented by centers of balls (not separately designated) of ball-and-socket joints 540, 546.

Figure 22:
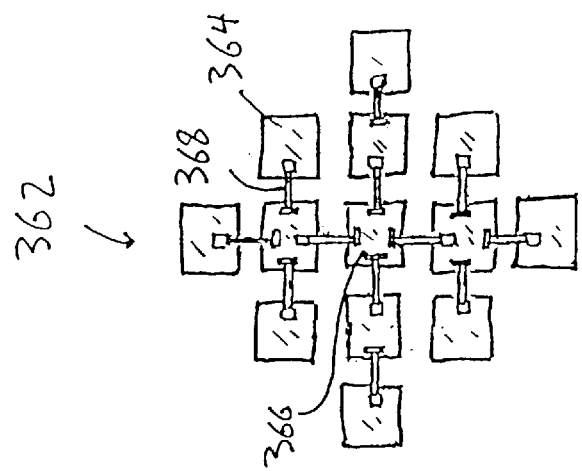
FIG. 22 is a schematic perspective view of a second mechanical armature utilizing the mechanical linkage of FIG. 15A.
Figure 25:
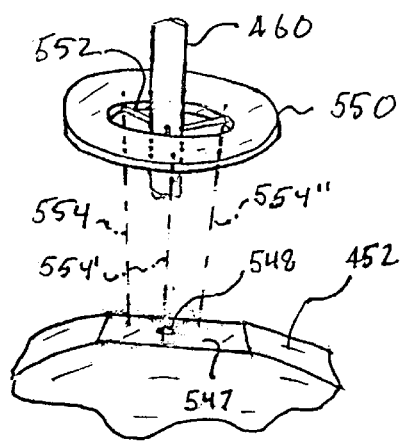
FIG. 25 is a detail perspective view showing a single mechanical linkage modified to incorporate laser interferometry (FIG. 23).

A method of employment of assembly 530 to permit measurement of six degrees of freedom or possible motions between rigid bodies is illustrated in FIG. 25. A rigid body such as plate 452 of FIG. 16 is provided with a land 547. Cylinder 460 is connected to body or plate 452 via a ball-and-socket joint (not shown for clarity) at an attachment site 548. A ring 550 is rigidly affixed to cylinder 460 via rods 552 et seq. Three lines 554, 554' and 554" are conceived between ring 550 and land 547. Along each of the lines an assembly 530 (not shown for clarity) is connected between ring 550 and land 547 by ball and socket joints as illustrated in FIG. 24. The ball-and-socket joint at site 548 allows cylinder 460 three degrees of rotational freedom with respect to plate 452, identified as angles $\psi$, $\theta$, $\omega$ in FIG. 17. Three independent measures of extension along lines 554, 554', 554" suffice to fix these angles. An additional three measures of extension similarly obtained with respect to a ring affixed to piston 462 of assembly 454 determine angles $\psi'$, $\theta'$, $\omega$ of FIG. 17. A redundancy in determination of $\omega$ compensates for freedom of rotation about an axis parallel to a longitudinal axis of assembly 454 at both ball joints 456 and 458: in this arrangement piston 462 is constrained not to posses rotational freedom with respect to cylinder 460. Six measures of extension as described above thereby account for five degrees of freedom; a final repetition of the electro-optical components of assembly 530 along piston and cylinder 462, 460 itself, measuring extension $\lambda$, completes a determination of six degrees of freedom or parameters between plates 452 and 452'. It will be noted that the combined metrologic apparatus of FIGS. 17, 22 and 23 is partially self-similar, a situation necessitated by the ability of laser interferometry to determine solely extensions, and not directly angles, and the simultaneous necessity to provide a rigid extensible assembly along each measured extension to maintain a laser line-of-sight. It will be readily appreciated by those skilled in the art that a simplification of the presently described metrologic scheme may be under-taken in connection with frames or mechanical skeletons such as those represent in FIGS. 18 and 19, the embodiment of FIGS. 17, 22 and 23 representing a most complex case, allowing a range of fully arbitrary movement between adjacent mounting or rigid bodies.

In case of a full freedom of movement of adjacent plates 452, 452', as shown in FIGS. 16 and 17, a full two-dimensional mechanical skeleton may be executed as shown in FIG. 16 without mechanical conflict. In the case a reduced number of degrees of freedom between adjacent plates, as shown in FIG. 18, a full two-dimensional armature or skeleton may still be executed in some cases, as shown in FIG. 19, provided due consideration is given to mechanical compatibility. In general however, given a sufficiently reduced number of degrees of freedom, as shown, for example, in FIG. 15A, it will not be possible to interconnect every pair of adjacent plates and maintain flexibility in the frame. In general a tree-structure will embody the greatest degree of mechanical interconnection possible while allowing independent movement in all existing joints. Examples of such structures are shown in FIGS. 21 and 22.

Figure 21:
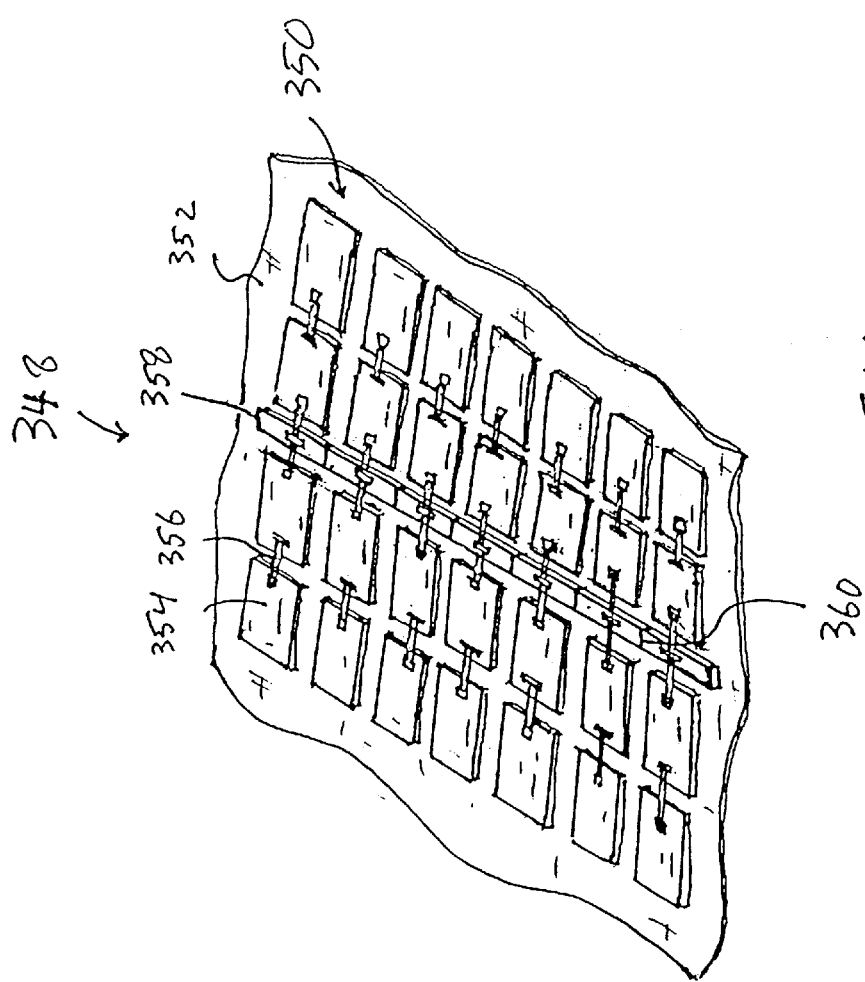
FIG. 21 is a schematic perspective view of a mechanical armature with fabric backing utilizing the linkage of FIG. 15A.

An employment of the mechanical linkage of FIG. 15A in an armature or skeleton 348 of an acoustic transducer carrier for an acoustic or ultrasonic imaging system is illustrated in FIG. 21. A flexible transducer array comprises a spine or central element 358 on which are affixed a plurality of side-arms 350. Side-arms 350 comprise one or more tiles or rigid mounting plates 354 connected by mechanical linkages 356 and forming a chain starting at the spine 358. Each linkage 356, comprising couplings 434, 436 and rod 438 of FIG. 15A, allows and encodes two degrees of mechanical freedom between adjacent tiles 354. Further hinges 360, in spine 358, each allow and encode a single degree of freedom. Armature 348 may advantageously be aligned along a dorsal or ventral axis of symmetry of a structural member. The armature may also be placed around a side of a structural member.

Yet another transducer-carrying armature or skeleton utilizing joints with two degrees of rotational freedom is illustrated in FIG. 22. Lacking a spine or other specialized structural element, tiles 364 connected by mechanical linkages 368 are arrayed in a symmetrical branching structure around a central tile or element 366. A symmetrical branching structure may be executed starting with any odd number of elements in a longest row, the number illustrated in FIG. 22 being "five". Such a skeleton or spider 362, realized at an appropriate scale and employing an external monitoring device (not shown), is useful for wrapping a highly curved portion of a load-bearing member, such as the leading edge of an airplane wing or tail.

Lower surface of tiles 354 and spine 358 (FIG. 21) are optionally affixed a web or flexible fabric backing 352 provided with openings for acoustic transducers mounted on the under surfaces of tiles 354. Backing 352 may be redoubled to cover a top surface or tiles 354 and spine 358, completely enclosing mechanical linkages 356 and ancillary electrical wiring (not shown). It is to be understood that a mechanical skeleton as shown in FIGS. 16, 19, 21 or 22 may in general be enclosed by a flexible fabric container with side panels in the form of webs or sheets (not shown) to protect exposed mechanical and electrical linkages from damage and interference.

Figure 26:
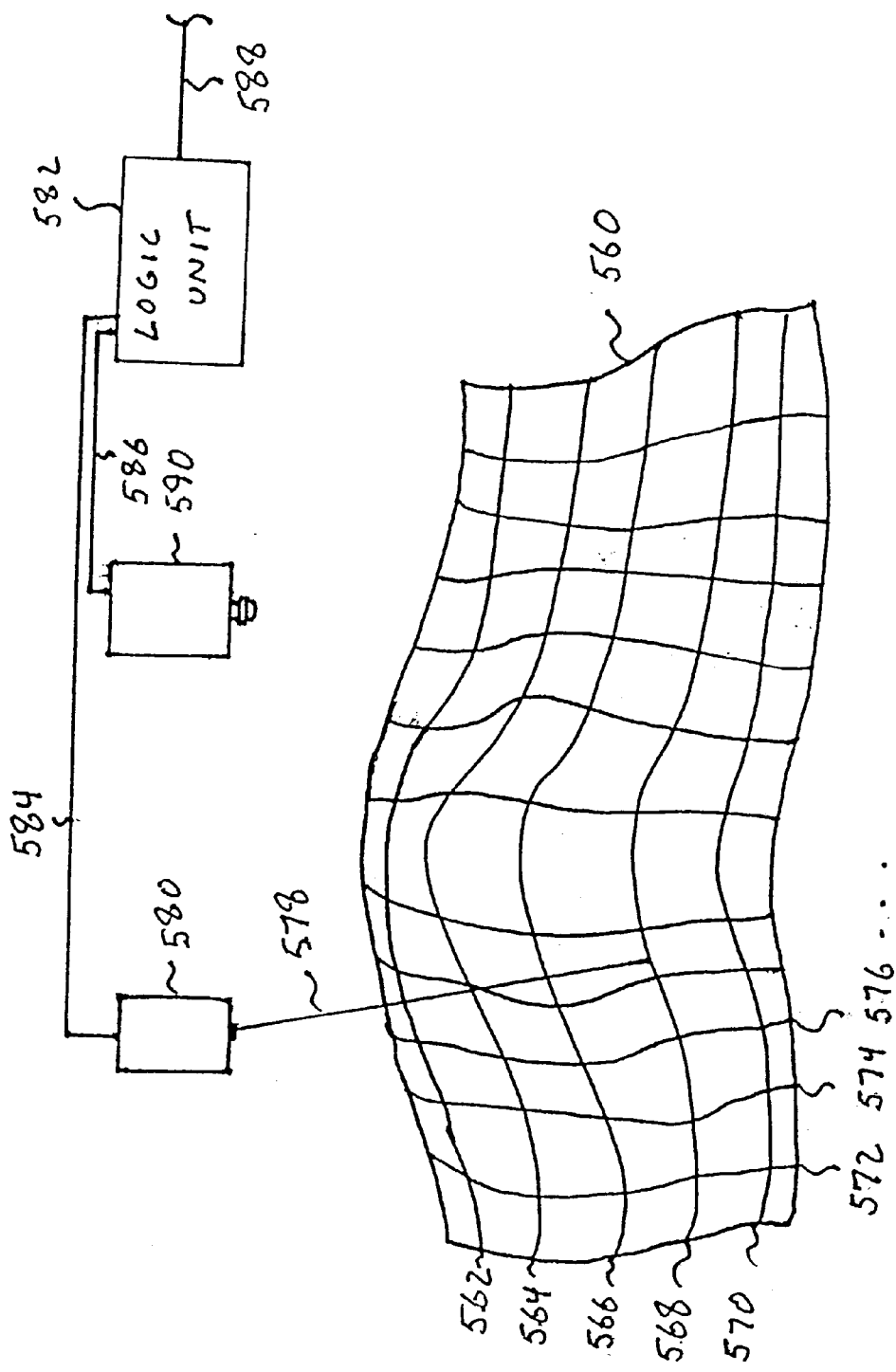
FIG. 26 is partially a schematic and partially a block functional diagram showing a system and a method of determining the shape of a surface by laser scanning.

An additional method for determining a shape of a major surface of a flexible substantially two-dimensional body, such as web or sheet 108, is illustrated in FIG. 26. A steerable switchable laser beam 578 is generated by a laser unit 580 in turn directed by a logic unit 582 via a data line 584 to scan a surface 560 in a rectangular grid pattern, represented by scan lines of a first orientation 562, 564, 566, 568, 570 and scan lines of a second orientation 572, 574, 576, etc. Because of departure from planarity by surface 560, scan lines 562 and 572 etc. in general depart from linearity, both in space and as imaged from a particular focal plane. In particular, lines 562 et alia depart from linearity as imaged in a focal plane of a digital camera 590. Unit 582 processes image data received from camera 590 via a data line 586 to deduce a shape of surface 560. Logic unit 582, digital camera 590 and laser unit 580 in this embodiment, along with associated software, comprise a particular realization of position determination module 284 of FIG. 11.

Figure 26A:
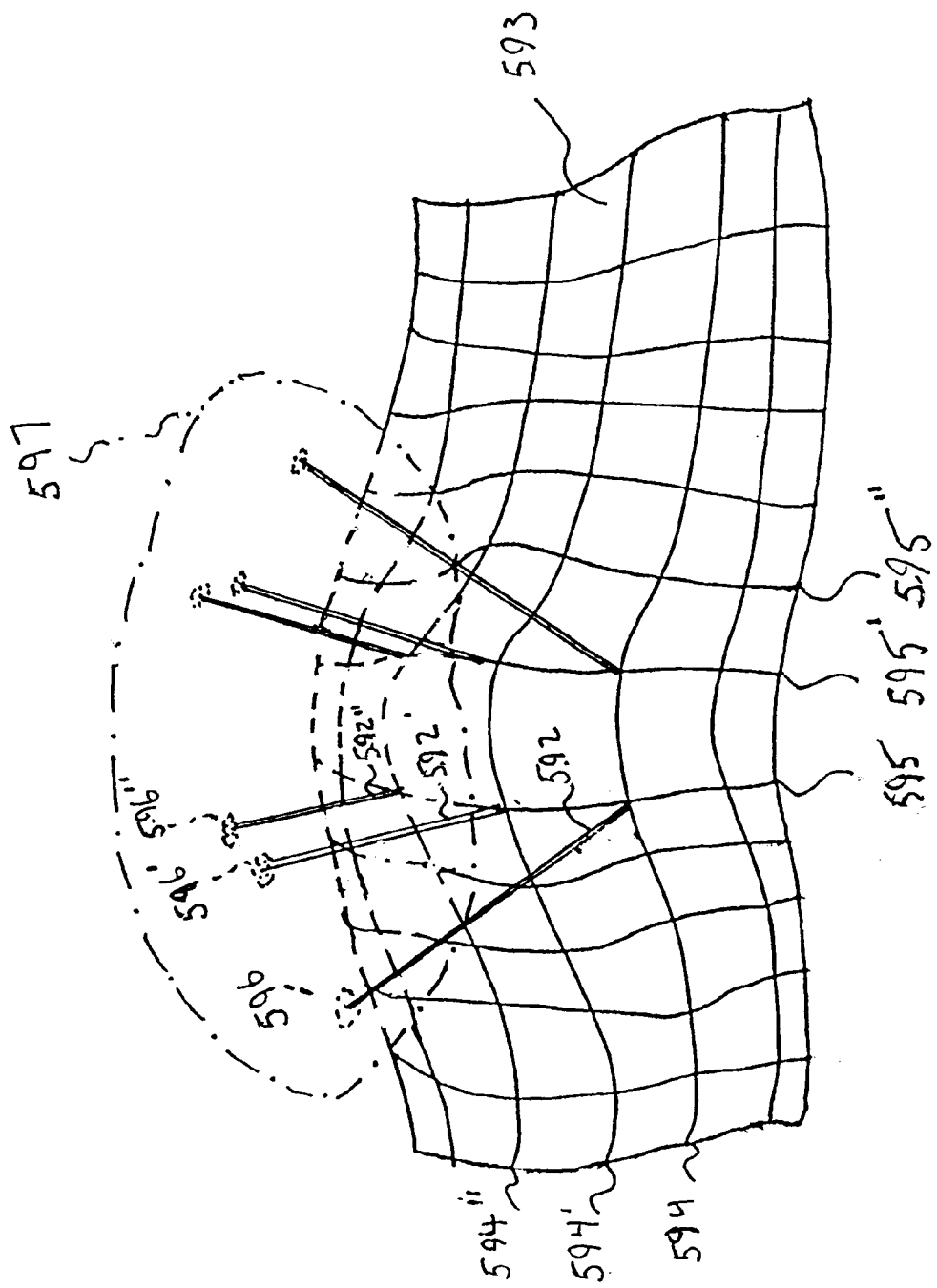
FIG. 26A is a schematic perspective view showing an alternative method of determining the shape of a surface by means of lasers.

A further method for determining a shape of a two dimensional surface via substantially normally pointing laser beams is shown in FIG. 26A. Laser beams 592, 592', 592" et al. originate from lasers (not shown) situated on intersections (not designated) of representative grid-lines 594, 594', 594" and 595, 595', 595" on a blanket or web 593. Grid lines 594, 595 et al. represent conceptual or actual structural features on web 593. The lasers are mounted in a rigid orientation, preferably normal, with respect to a surface of the web. Together with a substantial degree of rigidity of the web this rigid orientation is sufficient to establish the possibility of reconstructing a shape of web 593 from positions of spots 596, 596', 596" illuminated by the lasers on a screen 597, which screen may incorporate a fine sensor grid or photoreceptor array (not shown). Information about curvature of a surface is provided at a second overlying surface by this method much the way information about curvature of a porcupine's skin is conveyed by positions of the tips of its quills (not shown): Widely space quill tips are indicate of an underlying zone of convexity, while bunched together quill tip are indicative of an underlying concave region.

Although the invention has been described in terms of particular embodiments and applications, one of ordinary skill in the art, in light of this teaching, can generate additional embodiments and modifications without departing from the spirit of or exceeding the scope of the claimed invention. For example, buckles 128 and 130 may be replaced by other fastening elements, including clasps, hook and loop fasteners (VELCRO™), and hooks and eyelets.

Furthermore, although the invention has been disclosed particularly with respect to the use of ultrasonic pressure waves, many structural defects may be more appropriately discovered, diagnosed, and graphically displayed through the use of sonic waves (in an audible frequency range), either alone or in conjunction with ultrasonic pressure waves. These lower-frequency pressure waves may be generated via the piezoelectric transducers 114 and 116 disclosed herein. Alternatively or additionally, the energization waveforms transmitted into the structural member under testing may be generated by an ancillary device, for example, a hydraulically or pneumatically driven hammer mechanism. Such a wave generation mechanism generally produces an energization waveform which is a Fourier composite of a number of sinusoidals waveforms of differing frequencies. Some of these included waveforms may be in an ultrasonic frequency range. In any event, signal processor 120 and other wave analysis components disclosed herein are designed to process sonic-frequency signals as well as ultrasonic signals.

Accordingly, it is to be understood that the drawings and descriptions herein are proffered by way of example to facilitate comprehension of the invention and should not be construed to limit the scope thereof.

What is claimed is:

1. A method for investigating structural integrity, comprising:

providing a carrier member having a flexible surface, a plurality of electromechanical transducer elements being attached to said carrier member, said transducer elements being spaced from each other along at least two spatial dimensions;

conforming said flexible surface to a solid structural member, so that a substantial portion of said flexible member is in effective wave-transmitting engagement with said structural member;

after the conforming of said flexible surface to said structural member, transmitting pressure waves into said structural member;

receiving pressure waves reflected from an internal structural defect in said structural member in response to the pressure waves transmitted into said structural member; and analyzing the received pressure waves so as to detect said structural defect.

2. The method defined in claim 1, further comprising:

generating a signal encoding an image of said structural defect from the analyzed pressure waves; and presenting said image on a display.

3. The method defined in claim 2, further comprising operating a computer to highlight a selected feature of said structural defect on said display.

4. The method defined in claim 3 wherein the highlighting of said structural defect including varying video image intensity in a portion of a video image on said display.

5. The method defined in claim 2, further comprising operating a computer to select said image from among a multiplicity of possible images of said structural defect.

6. The method defined in claim 2, further comprising operating a filter stage to eliminate a selected artifact from said image.

7. The method defined in claim 1 wherein the analyzing of the received pressure waves includes operating a digital computer to derive a digital or electronic model of said structural defect.

8. The method defined in claim 7 wherein analyzing of the received pressure waves further includes operating said computer to perform an automated diagnosis or evaluation of said structural defect based in part on said digital or electronic model of said structural defect.

9. The method defined in claim 8 wherein the performance of said automated diagnosis or evaluation of said structural defect includes operating said computer to automatically compare said digital or electronic model with digital or electronic models of known structural defects stored in a memory of said computer.

10. The method defined in claim 1 wherein said carrier member includes a flexible web, said flexible surface being a surface of said web, the conforming of said flexible surface to said structural member including wrapping said web around at least a portion of said structural member.

11. The method defined in claim 10 wherein said transducer elements are mounted to said web, the conforming of said flexible surface to said structural member including placing said transducer elements in contact with said structural member.

12. The method defined in claim 1 wherein said carrier member includes at least one substantially rigid panel and a flexible web connected to said panel to form a bag along said panel, said flexible surface being a surface of said web, the conforming of said flexible surface to said structural member including placing said flexible web in contact with said structural member, the conforming of said flexible surface to said structural member further including feeding a fluid to said bag to press said web against said structural member.

13. The method defined in claim 12 wherein said transducer elements are mounted to said web, the conforming of said flexible surface to said structural member including placing said transducer elements in contact with said structural member.

14. The method defined in claim 12 wherein said panel is one of a plurality of panels, the conforming of said flexible surface to said structural member including placing said bag so that said flexible surface faces said structural member and so that said panels are disposed on an outer side of said bag, away from said structural member, the conforming of said flexible surface to said structural member further including fastening said panels to one another about said structural member to limit expansion of said bag upon feeding of said fluid thereto.

15. The method defined in claim 12 wherein at least some of said transducer elements are disposed on said panel, said fluid being a liquid, the transmitting of said pressure waves into said structural member including transmitting said pressure waves through said liquid in said bag.

16. The method defined in claim 1 wherein the conforming of said flexible surface to said structural member includes placing said flexible surface in engagement with at least two surfaces of said structural member extending at a substantial angle relative to one another.

17. The method defined in claim 1 wherein the conforming of said flexible surface to said structural member includes fastening said carrier member to said structural member.

18. The method defined in claim 1 wherein the analyzing of the received pressure waves includes determining therefrom a three-dimensional shape of said structural defect.

19. The method defined in claim 1 wherein the transmitting of said pressure waves into said structural member includes producing said pressure waves in a plurality of different frequency ranges, the receiving of pressure waves reflected from said structural defect including sensing pressure waves in said plurality of different frequency ranges.

20. The method defined in claim 1 wherein said transducer elements are mounted to said carrier member in a predetermined array, further comprising energizing said transducer elements in a predetermined sequence.

21. The method defined in claim 1 wherein the pressure waves transmitted into said structural member include ultrasonic frequency pressure waves.

22. An apparatus for investigating defects in structural members, comprising:

a carrier member having a flexible surface, said carrier member including a pressurizable bag for conforming said flexible surface to a solid structural member, so that a substantial portion of said flexible member is in effective wave-transmitting engagement with said structural member;

a plurality of electromechanical transducer elements attached to said carrier member, said transducer elements being spaced from each other along at least two spatial dimensions;

a frequency generator operatively connected to at least a given one of said transducer elements for energizing said given one of said transducer elements to transmit pressure waves into said structural member; and a frequency processor operatively connected to at least another one of said transducer elements to process pressure waves received by said another one of said transducer elements from an internal structural defect in said structural member in response to the pressure waves transmitted from said given one of said transducer elements, said processor including means for analyzing the received pressure waves to detect said structural defect.

23. The apparatus defined in claim 22, further comprising an expansion restrictor surrounding said bag for limiting outward expansion thereof in a direction opposite said structural member.

24. The apparatus defined in claim 23 wherein said expansion restriction includes a plurality of rigid panels movably connected to one another and locks of fasteners operatively connected to said panels.

25. The apparatus defined in claim 22, further comprising imaging means for generating a signal encoding an image of said structural defect from the analyzed pressure waves, said imaging means being operatively connected to a display for presenting said image to a viewer or operator.

26. The apparatus defined in claim 22 wherein said processor includes means for deriving a digital or electronic model of said structural defect from the analyzed pressure waves.

27. The apparatus defined in claim 26 wherein said processor further includes means for executing an automated diagnosis or evaluation of said structural defect based in part on said digital or electronic model of said structural defect.

28. The apparatus defined in claim 22 wherein said transducer elements are mounted to said bag along a flexible panel thereof.

* * * * *